(12) United States Patent
Gonda

(10) Patent No.: US 8,689,803 B2
(45) Date of Patent: *Apr. 8, 2014

(54) SYSTEMS AND METHODS FOR EFFECTING CESSATION OF TOBACCO USE

(75) Inventor: Igor Gonda, San Francisco, CA (US)

(73) Assignee: Aradigm Corporation, Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/562,786

(22) Filed: Jul. 31, 2012

(65) Prior Publication Data

US 2012/0305011 A1 Dec. 6, 2012

Related U.S. Application Data

(60) Continuation of application No. 11/932,437, filed on Oct. 31, 2007, now Pat. No. 8,256,433, and a continuation-in-part of application No. 11/097,598, filed on Apr. 1, 2005, now abandoned, which is a continuation of application No. 10/913,103, filed on Aug. 6, 2004, now Pat. No. 6,874,507, which is a division of application No. 10/147,390, filed on May 15, 2002, now Pat. No. 6,799,576, which is a continuation-in-part of application No. 09/611,423, filed on Jul. 7, 2000, now abandoned.

(60) Provisional application No. 60/982,070, filed on Oct. 23, 2007, provisional application No. 60/868,238, filed on Dec. 1, 2006, provisional application No. 60/911,044, filed on Apr. 10, 2007, provisional application No. 60/913,185, filed on Apr. 20, 2007, provisional application No. 60/916,510, filed on May 7, 2007, provisional application No. 60/917,190, filed on May 10, 2007, provisional application No. 60/144,140, filed on Jul. 16, 1999.

(51) Int. Cl.
*A24F 47/00* (2006.01)
*A62B 9/00* (2006.01)

(52) U.S. Cl.
USPC ..................... 131/270; 128/200.24

(58) Field of Classification Search
USPC ..................... 131/270; 128/200.24
See application file for complete search history.

(56) References Cited

U.S. PATENT DOCUMENTS

| | | | |
|---|---|---|---|
| 3,439,685 A | 4/1969 | Allen | |
| 4,146,040 A | 3/1979 | Cohn | |
| 4,284,089 A | 8/1981 | Ray | |
| 4,393,884 A | 7/1983 | Jacobs | |
| 4,463,770 A | 8/1984 | Thompson | |
| 4,474,191 A | 10/1984 | Steiner | |
| 4,579,858 A | 4/1986 | Ferno et al. | |
| 4,635,651 A | 1/1987 | Jacobs | |
| 4,715,387 A | 12/1987 | Rose | |
| 4,735,217 A | 4/1988 | Gerth et al. | |
| 4,765,348 A | 8/1988 | Honeycutt | |
| 4,793,366 A | 12/1988 | Hill | |
| 4,800,903 A | 1/1989 | Ray et al. | |
| 4,813,437 A | 3/1989 | Ray | |
| 4,917,120 A | 4/1990 | Hill | |
| 4,934,358 A | 6/1990 | Nilsson et al. | |
| 4,945,929 A | 8/1990 | Eglimex | |
| 4,953,572 A | 9/1990 | Rose et al. | |
| 5,051,426 A | 9/1991 | Parnell | |
| 5,167,242 A | 12/1992 | Turner et al. | |
| 5,362,496 A | 11/1994 | Baker et al. | |
| 5,400,808 A | 3/1995 | Turner et al. | |
| 5,441,060 A | 8/1995 | Rose et al. | |
| 5,501,236 A | 3/1996 | Hill et al. | |
| 5,654,000 A | 8/1997 | Poli et al. | |
| 5,721,257 A | 2/1998 | Baker et al. | |
| 5,746,227 A | 5/1998 | Rose et al. | |
| 5,810,018 A | 9/1998 | Monte | |
| 5,823,178 A | 10/1998 | Lloyd et al. | |
| 5,824,334 A | 10/1998 | Stanley | |
| 5,834,011 A | 11/1998 | Rose et al. | |
| 5,845,647 A | 12/1998 | O'Donnell et al. | |
| 5,894,841 A | 4/1999 | Voges | |
| 5,906,202 A | 5/1999 | Schuster et al. | |
| 5,935,604 A | 8/1999 | Illum | |
| 5,939,100 A | 8/1999 | Albrechtsen et al. | |
| 6,004,970 A | 12/1999 | O'Malley et al. | |
| 6,024,097 A | 2/2000 | Von Wielligh | |
| 6,196,218 B1 | 3/2001 | Voges | |
| 6,413,496 B1 | 7/2002 | Goodman et al. | |
| 6,759,435 B1 | 7/2004 | Chen | |
| 6,799,576 B2 | 10/2004 | Farr | |

(Continued)

FOREIGN PATENT DOCUMENTS

DE 32 41 437 A1 5/1984
EP 0 557 129 8/1993

(Continued)

OTHER PUBLICATIONS

Clarke, "Nicotine dependence—mechanisms and therapeutic strategies," Biochem. Soc. Symp., 59:83-95 (1992).
Henningfield, "Nicotine Medications for Smoking Cessation" The New England Journal of Medicine, 333 (18):1196-1203 (1995).
Maurer et al., "Therapeutic vaccines for nicotine dependence" Current Opinion in Molecular Therapeutics (2008) 8 (1):11-16.
Moreno et al., "Immunopharmacotherapy: Vaccination Strategies as a Treatment for Drug Abuse and Dependence" Pharmacol. Biochem. Behav. (Apr. 2009) 92(2):199-205.

(Continued)

*Primary Examiner* — Philip Tucker
*Assistant Examiner* — Dionne Walls Mayes
(74) *Attorney, Agent, or Firm* — Karl Bozicevic; Bozicevic, Field & Francis LLP

(57) ABSTRACT

The invention relates generally to a system and method for treating conditions responsive to nicotine therapy. More specifically, the invention relates to pulmonary administration of a nicotine containing formulation to effect smoking cessation.

13 Claims, 4 Drawing Sheets

(56) References Cited

U.S. PATENT DOCUMENTS

| | | | |
|---|---|---|---|
| 8,256,433 B2 * | 9/2012 | Gonda | 131/271 |
| 8,381,739 B2 * | 2/2013 | Gonda | 131/270 |
| 2002/0094998 A1 | 7/2002 | Chappell et al. | |
| 2003/0109544 A1 | 6/2003 | Harrigan et al. | |
| 2003/0159702 A1 | 8/2003 | Lindell et al. | |
| 2003/0171408 A1 | 9/2003 | Caplan | |
| 2003/0235589 A1 | 12/2003 | Demopulos et al. | |
| 2004/0037879 A1 | 2/2004 | Adusumilli et al. | |
| 2005/0069518 A1 | 3/2005 | Mousa et al. | |
| 2007/0099999 A1 | 5/2007 | Epstein et al. | |
| 2011/0182918 A1 | 7/2011 | Kalnik et al. | |

FOREIGN PATENT DOCUMENTS

| | | |
|---|---|---|
| GB | 1162314 | 8/1969 |
| GB | 2 191 718 A | 12/1987 |
| JP | 5-507639 | 11/1993 |
| JP | 6-315367 | 11/1994 |
| JP | 7-506981 | 8/1995 |
| JP | 10-508230 | 8/1998 |
| WO | 91/18636 | 12/1991 |
| WO | 93/16748 | 9/1993 |
| WO | 94/27576 | 12/1994 |
| WO | 96/13292 | 5/1996 |
| WO | 97/12639 | 4/1997 |
| WO | 99/15171 | 4/1999 |
| WO | 99/45902 | 9/1999 |
| WO | 01/05459 | 1/2001 |
| WO | 03/097146 | 11/2003 |

OTHER PUBLICATIONS

Sutherland et al., "Nasal Nicotine Spray: A Rapid Nicotine Delivery System" Psychopharmacology, 108:512-518 (1992).

* cited by examiner

Modified Fagerström Test for Nicotine Dependence

1. How soon after you wake up do you smoke your first cigarette?
Within 5 minutes (3 points)
5 to 30 minutes (2 points)
31 to 60 minutes (1 point)
After 60 minutes (0 points)

2. Do you find it difficult not to smoke in places where you shouldn't, such as in church or school, in a movie, at the library, on a bus, in court or in a hospital?
Yes (1 point)
No (0 points)

3. Which cigarette would you most hate to give up; which cigarette do you treasure the most?
The first one in the morning (1 point)
Any other one (0 points)

4. How many cigarettes do you smoke each day?
10 or fewer (0 points)
11 to 20 (1 point)
21 to 30 (2 points)
31 or more (3 points)

5. Do you smoke more during the first few hours after waking up than during the rest of the day?
Yes (1 point)
No (0 points)

6. Do you still smoke if you are so sick that you are in bed most of the day, or if you have a cold or the flu and have trouble breathing?
Yes (1 point)
No (0 points)

Scoring: 7 to 10 points = highly dependent; 4 to 6 points = moderately dependent; less than 4 points = minimally dependent.

FIG. 4

SYSTEMS AND METHODS FOR EFFECTING CESSATION OF TOBACCO USE

PRIORITY DOCUMENTS

This application is a continuation of U.S. patent application Ser. No. 11/932,437, filed Oct. 31, 2007 issued Sep. 4, 2012, as U.S. Pat. No. 8,256,433, which application claims the benefit of U.S. Provisional Application Nos. 60/982,070, filed Oct. 23, 2007; 60/868,238, filed Dec. 1, 2006; 60/911,044, filed Apr. 10, 2007; 60/913,185, filed Apr. 20, 2007; 60/916,510, filed May 7, 2007; and 60/917,190, filed May 10, 2007 and is a continuation-in-part of U.S. application Ser. No. 11/097,598 filed on Apr. 1, 2005 now abandoned which is a continuation of Ser. No. 10/913,103, filed Aug. 6, 2004, issued Apr. 5, 2005, as U.S. Pat. No. 6,874,507, which is a divisional of 10/147,390, filed May 15, 2002, issued Oct. 5, 2004, as U.S. Pat. No. 6,799,576, which is a continuation-in-part of 09/611,423, filed Jul. 7, 2000, now abandoned, which claims benefit to U.S. Provisional Application No. 60/144,140 filed on Jul. 16, 1999, all of which applications are incorporated herein by reference.

FIELD OF THE INVENTION

The invention relates generally to a method and formulation for treating conditions responsive to nicotine therapy. More specifically, the invention relates to pulmonary administration of a nicotine containing formulation to effect nicotine addiction related to the use of tobacco products.

BACKGROUND

Diseases related to cigarette smoking and other forms of tobacco consumption, such as lung disease, heart disease and cancer, claim an estimated 400,000 lives each year. The combustion of tobacco produces poisons and carcinogens that present a significant health hazard for smokers and non-smokers alike. Nicotine is a principal component of tobacco, and the most pharmacologically active. It is physically addictive, making it extremely difficult for a smoker to quit.

Smoking a cigarette delivers nicotine directly to the lungs, where nicotine is rapidly absorbed through the arteries and delivered to the brain. Nicotine interacts with nicotinic cholinergic receptors in the brain to induce the release of neurotransmitters and produce an immediate reward—the "rush" that smokers experience—that is associated with a rapid rise in blood level. A persistent stimulus is also produced, and is associated with a high blood level of nicotine. As such, the dopaminergic reward system is activated which eventually results in nicotine dependency. Complex behavioral and social aspects of smoking, e.g., the hand-to-mouth ritual, etc., are also habit-forming.

A therapeutic approach to aid in smoking cessation and other forms of nicotine addiction is to provide the patient with nicotine from sources other than tobacco. Nicotine can be administered orally. However, after oral administration it is absorbed from the gut into the portal blood and degraded promptly by the liver. Nicotine can also be administered parenterally, e.g., intravenously, transcutaneously, mucosally, etc. Although preparations of nicotine appropriate for intravenous administration have been available for some time, intravenous cannulation as a means for gaining access to the circulation for the administration of nicotine on demand is not a socially acceptable alternative to cigarette smoking. There are also a number of commercially available nicotine replacement therapies that deliver nicotine to the systemic circulation via absorption through mucosal membranes or the skin. These include nicotine-containing chewing gum, sachets, transdermal patches, capsules, tablets, lozenges, nasal sprays and oral inhalation devices.

In particular, nicotine delivery via inhalation offers the benefit of addressing the psychological component of cigarette, cigar, and pipe smoking in addition to the physiological dependence on nicotine. Nicotine inhalation systems release nicotine as a vapor (see U.S. Pat. Nos. 5,167,242; 5,400,808; 5,501,236; 4,800,903; 4,284,089; 4,917,120; 4,793,366), aerosol (see U.S. Pat. Nos. 5,894,841; 5,834,011) or dry powder (see U.S. Pat. No. 5,746,227) when air is inhaled through the inhaler. A droplet ejection device (U.S. Pat. No. 5,894,841) has also been described that delivers a controlled dose of nicotine via inhalation. These systems deliver low doses of nicotine to the mouth and throat, where nicotine is absorbed through the mucosal membranes into the circulation. Some inhalation therapies feature devices that simulate or approximate the look, feel and taste of cigarettes.

Currently available nicotine replacement therapies, such as transdermal and buccal systems where absorption occurs slowly, provide a low, steady-state blood level of nicotine to the patient without the early nicotine concentration spike that provides a smoker immediate, arterial delivery of nicotine to the brain. Thus, the goal of these therapies is to eliminate the immediate, pleasurable effects associated with smoking while still alleviating the nicotine withdrawal effects until complete cessation of nicotine is physically and psychologically possible for the patient. The perceived advantage of these therapies is that the likelihood of abusing the nicotine delivery device (e.g., transdermal patch, nicotine chewing gum, nicotine inhalers, etc.) is very low. However, it is believed by some that it is because of this complete lack of "rush" experienced by the patient, that the success rates of these conventional therapies are not higher than they are.

Thus, the need remains for a smoking cessation therapy that delivers a precise dose of nicotine directly to the lungs and, therefore, directly into the arterial circulation in a profile that mimics the blood levels achieved by smoking—providing an initial sharp rise in blood level making it possible for the user to be weaned off of nicotine and to quit smoking.

SUMMARY

The invention includes a systems and methods for quickly raising a patient's plasma level of a nicotine formulation and thereafter gradually reducing the peak plasma level in order to reduce the patient's craving for the drug. The invention is also applicable to other addictive drugs such as narcotics, etc. Methods of the invention are typically carried out using a system that includes a plurality of groups of containers wherein each container within a group provides substantially the same maximum plasma concentration of the drug. Subsequently used groups of containers allow the patient to titrate the dose to an optimal level to eliminate their acute cravings. After the patient is able to replace cigarettes, or any other form of tobacco, with an inhaled nicotine formulation they will enter a treatment phase designed to reduce the maximum concentration of the drug in the plasma in a gradual manner so as to wean the patient off of the drug. The weaning process can be carried out in a number of different ways, each of which results in a gradual reduction in the peak plasma level. For example, formulations within the different groups can have decreasing amounts or concentrations of the drug such as nicotine or morphine. It is also possible to reduce the peak plasma level by increasing the particle size of the aerosol created in order to move the deposition of the drug to a higher level of the respiratory tract and thereby reduce the overall rate of absorption leading to a reduction in peak plasma level. It is also possible to include the drug within a formulation which provides for a delayed or controlled release of the drug which again leads to a reduction in the peak plasma level. Other adjustments in the formulation are possible such as reducing the pH in that higher pH formulations (more basic) tend to be absorbed more quickly as compared to lower peak formulations. All or any of these parameters can be varied individually or together with any other in order to obtain a desired result.

Alternatively, it may be beneficial to deliver a lower dose of nicotine to the patient using the system of the invention. This approach may be used for example to accustom the patient to use of the system and to protect the patient from possible adverse effects of applying larger doses of pure nicotine from the onset of treatment. The nicotine dose may be increased with time, thereby replacing the nicotine acquired from the cigarette. Once the patient is weaned from the cigarettes, the dosage supplied by the system of the invention may be decreased to alleviate the nicotine addition itself.

By optionally providing a large dose of nicotine in a single inhalation, the present invention mimics the nicotine delivery of a cigarette. A single inhalation may provide either a single dose of nicotine equivalent to that contained in an entire cigarette or a more complex formulation that provides both a rapid- and sustained release of nicotine. Through the use of two forms of nicotine, nicotine delivery using a more complex formulation is even more pharmacologically similar to that presented by a cigarette. Smoking provides a large dose of nicotine to the smoker during a short period of time. This can not be obtained with a conventional gum or patch nicotine delivery system. As a result the patient often reverts to smoking to obtain the necessary high peak level of nicotine. The present invention can be used in combination with a steady state delivery system (e.g. gum or patch) in order to satisfy the short term craving of the patient. Rather than reverting to smoking which provides nicotine together with numerous other potentially harmful compounds the delivery system of the present invention would provide pharmaceutical grade nicotine by itself in a pharmaceutically acceptable carrier. The system would reduce the number of cases of people treating short term craving by reverting to cigarette smoking. By using the invention to gradually reduce the plasma levels necessary to satisfy the craving the overall system leads to permanent elimination of cravings allowing the patient to break their nicotine addiction.

The invention includes a system for aiding a patient quit smoking which system can include a plurality of containers provided in groups of containers along with a device for aerosolizing formulation in the containers.

The nicotine formulations can be loaded into drug delivery devices which provide for aerosolized delivery of the formulation. The device can be designed so as to avoid overdosing such as by restricting the number of doses and/or the interval between doses. The device can also force the patient to reduce the frequency of administration by providing time lock-outs and provide rewards for reducing the number of uses. The device can be coordinated with containers and force the patient to use containers which provide lower peak plasma levels. Still further, the physician can be provided with programming authorization which can make it possible to program the device individually for the patient and obtain the most desirable results in terms of weaning the patient off of the drug.

An aerosol drug delivery device of the invention can also be programmed in order to record information with respect to a range of different parameters. For example, the device can electronically record the date and time of drug delivery and can specifically indicate the dose administered by electronically matching the delivery with an electronic indication on the drug packet inserted into the device. Other parameters can also be recorded such as the average time between dosing for the patient. By using such information it is possible to determine if the patient is moving in a positive direction towards reducing the frequency of the use of the device. This information can be tied to a reward system whereby the patient is provided with rewards when the system calculates that, on average, the frequency of use is decreasing and/or the dose required to satisfy the patient's craving is reduced. The device can also be designed to allow the patient to enter information such as where the patient was and the circumstances under which the cravings increased. Such information could be used in combination with counseling in order to determine how to best treat the patient.

A formulation comprised of nicotine, as well as a system for aiding a patient in quitting smoking is disclosed. The amount of nicotine aerosolized or effectively delivered to the patient can be changed in several different ways using devices of the system, the formulation, or formulation containers loaded into the devices.

A preferred system of the invention aerosolizes liquid nicotine formulation by applying force to a container of nicotine formulation and causing the nicotine formulation to be moved through a porous membrane which results in creating particles of nicotine formulation which are inhaled by the patient. Such a system is referred to here as a unit dose solution aerosolizer. Examples are described in U.S. Pat. No. 5,544,646. This system modifies the amount of nicotine aerosolized by providing a plurality of different containers or different groups of containers wherein the different containers or groups of containers contain different concentrations of nicotine. A patient using the system can utilize packets of nicotine formulation containing a high concentration initially and then gradually switch towards lower and lower concentrations so that the patient receives essentially the same amount of aerosolized formulation but receives gradually reduced amounts of nicotine due to the reduced concentration of the nicotine in the formulation.

The same procedure described above can also be carried out with a dry powder inhaler (DPI). Using the dry powder inhaler technology the packets of dry powder nicotine formulation loaded into the device can initially contain a relatively high concentration of nicotine. Thereafter, the concentration of nicotine in the dry powder formulation added into the device is gradually changed. Thus, using this system the same amount of dry powder is aerosolized, but the amount of nicotine is gradually increased or decreased by increasing/decreasing the concentration or simply the total amount of nicotine in the dry powder package loaded into the device. In either case, the patient might benefit from concomitant therapy with an antidepressant or anxiolytic to reduce the psychological effects of nicotine withdrawal.

Additionally, the same procedure can be utilized with a conventional metered dose inhaler (MDI) device. Small pressurized canisters conventionally used with MDIs can contain different concentrations of nicotine along with the propellant. Again, the patient might benefit from concomitant therapy with an antidepressant or anxiolytic to reduce the psychological effects of nicotine withdrawal.

Yet another means to achieve gradually lower peak plasma levels of nicotine is by reducing the deposition in the lung, especially in the "deep" lung. This can be achieved by changing the particle or droplet size produced by MDIs. This can be achieved through increasing the valve orifice in the MDI, or by changing the formulation, e.g., by increasing the concentration of non-volatile components.

When using a dry powder inhaler, an MDI, or a system which aerosolizes a liquid formulation by moving the formulation through a porous membrane, it is possible to decrease the amount of nicotine gradually by making changes in the device, or more specifically the operation of the device. For example, a dry powder inhaler often utilizes a burst of air in order to aerosolize the dry powder. The burst of air could be decreased so that not all of the powder is fully aerosolized or so that the powder is not aerosolized in a completely efficient manner. Or one can increase the particle size of the powder, or reduce the efficiency of their dispersion by using a variety of excipients available for this purpose.

When using an MDI the valve opening size and/or the amount of time the valve is opened to release aerosol can be changed as can the formulation in the device.

In a more preferred embodiment the system for aerosolizing liquid formulation is adjusted at different points so that different amounts of nicotine are aerosolized and the patient can be gradually weaned off of nicotine. As the "craving" is thought to be related to the peak plasma levels of nicotine, reducing the amount and/or moving the site of deposition of nicotine loaded droplets through droplet size engineering to reduce the extent and rate of absorption from the respiratory tract are ways of gradually weaning the smokers of their habit.

One embodiment of the invention involves the use of a system which aerosolizes liquid formulations of nicotine contained within individual packets which packets include a porous membrane. As indicated above the rate and amount of nicotine that can be absorbed is varied by changing the amount of, concentration of and/or pH of the nicotine in the packets. However, it is also possible to decrease the amount of nicotine actually delivered to the patient's circulatory system by changing the size of the pores in the membrane. When the pore size is in a preferred range then a relatively high amount of the formulation aerosolized will reach the patient's deep lungs and rapidly move from the lungs into the patient's circulatory system. However, by making the pores larger the aerosolized particles created also become larger. The larger particles will not move into the deep lungs as efficiently as the smaller particles. For example, with oral inhalation at high to moderate inspiratory flow rates, a significant number of particles with aerodynamic size greater than 5 micron would deposit in the oropharynx from where they are not rapidly absorbed into the patient's circulatory system.

The pH of the formulation can be set at any desired level which is not damaging to lung surfaces. Although it is desirable to have a low pH formulation (acidic) to avoid interaction with certain types of plastic containers it is generally more desirable to have a high pH formulation (basic) to increase the absorption of the nicotine from the lung into the circulatory system. A patient could be dosed initially on a high pH formulation which provides for a more rapid and complete infusion of the nicotine into the circulatory system as compared to a low pH formulation. The patient could then be weaned off of the high pH formulation toward a neutral pH and finally toward a low pH formulation. Thus, for example, the patient could be initially dosed on a formulation with a pH of 9 which is later reduced to 8 and thereafter reduced to 7, 6 and 5. Other variations and incremental changes in the pH are also possible with the caveat that the formulation, when deposited within the respiratory tract, is not causing changes in the local pH that would damage lung surfaces.

Adjustments in the pH can be carried out alone or in combination with adjustments in the concentration of nicotine in the formulation. Either or both of these parameters can be changed in combination with changing the particle size of the aerosol created. A formulation with a higher concentration of nicotine, of course, provides more nicotine to the patient provided the same amount of formulation is aerosolized. By increasing the particle size the particles will generally deposit higher up in the patient's respiratory tract which slows the extent and the rate of absorption of the nicotine and leads to a reduction in peak levels of a patient's nicotine plasma level. Still further, it is possible to vary all or any of these parameters in combination with a formulation which provides for a controlled release of the nicotine. Thus, for example, the nicotine can be encapsulated in some manner or included with an excipient which provides for a more controlled release as compared to an immediate release formulation.

In one embodiment of the invention, a plurality of different groups of containers are produced. The groups of containers are different from each other in that they contain different amounts of nicotine, concentrations and/or formulations with different pHs. Alternatively, the groups of containers are different from each other in that they have different porous membranes on them which make it possible to aerosolize the formulation in a somewhat less efficient manner over time, or with particle size that leads to a deposition pattern in the body that in turn yields slower absorption and lower peak plasma levels of nicotine. It is possible to combine all or any of these features together. More specifically, it is possible to produce groups of containers which contain (1) varying concentrations of nicotine; (2) varying amounts of nicotine; (3) varying pH formulation; or (4) have porous membranes which have different size or amounts of pores so as to more or less efficiently aerosolize the formulation present in the container or that produce droplets or particles that deposit in a manner in which nicotine is absorbed less effectively and at a lower or higher rate.

It is desirable to combine these features optimally so that initially the nicotine inhalation system produces plasma levels of nicotine that mimic those following cigarette smoking so that the initial craving is satisfied but gradually the system uses groups of containers to reduce the plasma nicotine levels to wean off the subjects from the nicotine addiction.

A method for aiding in smoking cessation and for treating conditions responsive to nicotine therapy by the administration of nicotine is disclosed. A formulation comprised of nicotine is aerosolized. The aerosol is inhaled into the lungs of the patient. Once inhaled, particles of nicotine deposit on lung tissue and, from there, enter the patient's circulatory system. Because delivery is to the lungs, rather than to the oral mucosa or through the skin, the nicotine is immediately delivered, along with freshly oxygenated blood, to the heart via the pulmonary arteries where it is then pumped via the aorta to the arterial circulatory system, which is responsible for the delivery of oxygenated blood to the patient's entire body. The carotid arteries, in particular, transport the nicotine-containing oxygenated blood directly to the brain where it is then perfused throughout the brain by the neurovasculature system. Thus, the patient's serum nicotine level in the brain is quickly raised to a desired level—as quickly as if the user were smoking, providing the "rush" effect. The smoker is not immediately deprived of the psychological pleasures of smoking and, as such, is more likely to successfully complete the smoking-cessation treatment. Because the methods of the invention substantially bypass the body's processes that would effectively metabolize (e.g., by the liver) or dilute (e.g., by systemic distribution via the venous circulatory system) the nicotine dose and thus minimize the effect of the nicotine dose prior to delivery to the brain, the inventive methodologies are able to produce arterial plasma concentrations of nicotine similar to those experienced during cigarette smoking.

Subsequently, the patient's dependence on nicotine is reduced by gradually changing one or more parameters to move the patient away from needing any nicotine in any form. For example, the dose of nicotine delivered to the deep lung, from which it is absorbed most rapidly, is reduced by progressively increasing the size distribution of the aerosolized nicotine particles delivered to the patient. This decreases the amount of nicotine delivered to the patient's lungs, with the result that nicotine absorption is slower and the peak nicotine blood plasma level is lower.

A method of treatment is disclosed, comprising:

(a) aerosolizing a formulation comprised of nicotine creating aerosolized particles which are sufficiently small as to enter the alveolar ducts;

(b) allowing a patient to inhale the aerosolized particles of (a) thereby causing nicotine to enter the patient's blood at air/blood diffusion membranes;

(c) repeating (a) and (b) a plurality of times;

(d) aerosolizing a formulation comprised of nicotine creating aerosolized particles which are too large to enter predominantly alveolar ducts but sufficiently small to enter primary and secondary bronchioles;

(e) allowing the patient to inhale the aerosolized particles of (d) predominantly into primary and secondary bronchioles; and (f) repeating (d) and (e) a plurality of times.

The method is preferably further comprised of:

(g) aerosolizing a formulation comprised of nicotine creating aerosolized particles which are too large to enter predominantly primary and secondary bronchioles but sufficiently small to enter the small bronchi;

(h) allowing the patient to inhale the aerosolized particles that deposit predominantly into small bronchi; and (i) repeating (g) and (h) a plurality of times.

Although the devices and methods of the invention can be configured in order to target certain areas of the respiratory tract, it will be understood by those skilled in the art that it will not be possible to provide a system or produce a method which exclusively administers particles only to a particular area of a respiratory tract. In general, smaller size particles will deposit in the lung more deeply as compared to larger size particles. Further, it is generally not desirable to make the particles smaller than 0.5 micron in that the particles which are very small can be inhaled and exhaled back out without being deposited at all, unless the subject holds their breath for sufficient length of time, typically several seconds, for those particles to deposit. Further, it is generally not desirable to make the particles larger than 12 microns in that particles which are larger than this size generally deposit very high up in the respiratory tract and as such do not reach the blood quickly. When referring to targeting an area of the respiratory tract those skilled in the art will understand that it is matter of probabilities of deposition and that those probabilities can vary based on the size of the particles. It is also understood by those skilled in the art that aerosol particles often do not have a stable size. For example, droplets can pick up moisture for the air in the respiratory tract and grow in size; soluble particles can also pick up moisture, dissolve partly or entirely, and grow in size. Volatile components of droplets can evaporate and make the droplet size smaller. These changes may also cause changes in the density of the particles that affects their aerodynamic size. The important aspect here is to keep changing the deposition pattern during the therapy in such a way that the peak plasma concentrations of nicotine are gradually decreased.

Another method of treatment is disclosed which includes the steps of:

(a) aerosolizing a pharmaceutical formulation comprised of nicotine to create aerosolized particles having a size in the range from about 0.5 to 12 µm; and (b) allowing the patient to inhale the aerosolized particles of (a) thereby causing nicotine to directly enter the patient's arterial system from the patient's lungs.

The method may further include the step of:

(c) repeating steps (a) and (b) a plurality of times.

In certain embodiments, this method may further include the steps of:

(d) performing step (c) over a first period of time wherein the nicotine is present in a first amount and/or concentration; and (e) performing step (c) over a second period of time wherein the nicotine is present in a second amount and/or concentration which is different than the first amount and/or concentration.

In other embodiments, this method may further include the steps of:

d) performing step (c) over a first period of time wherein the aerosolized particles have a first size; and e) performing step (c) over a second period of time wherein the aerosolized particles have a second size which is different than the first size.

An aspect of the invention is a method of treatment whereby nicotine or a nicotine substitute is aerosolized, inhaled into areas of the respiratory tract including the lungs and provided to the arterial circulatory system of the patient at levels sufficient to simulate cigarette smoking.

An aspect of the invention is that the nicotine levels are raised almost immediately upon administration.

Another aspect of the invention is that the patient can gradually be weaned off of the immediate effect of nicotine obtained via smoking and gradually weaned off of the need of nicotine by, respectively, increasing particle size, decreasing dose size, concentration, or number of doses.

Still another aspect of the invention is that aerosolized particles of nicotine having a aerodynamic diameter of about 0.5 to 8 microns (µ) are created and inhaled deeply into the lungs, thereby enhancing the speed and efficiency of administration.

It is an aspect of this invention to describe the utility of delivering nicotine by inhalation as a means of treating conditions responsive to nicotine therapy, and particularly for smoking cessation therapy.

It is an aspect of this invention to describe the utility of varying the distribution of aerosolized particles of nicotine inhaled as a means of treating smokers wishing to quit.

It is another aspect of this invention to describe liquid formulations (which includes suspensions and other semiliquid forms) of nicotine and derivatives thereof appropriate for pulmonary delivery.

It is another aspect of this invention to describe how nicotine delivered via the lung can quickly increase arterial nicotine blood plasma concentration levels.

An aspect of the invention is a method whereby larger and larger particles of aerosolized nicotine are administered to a patient over time in order to first wean a smoking patient off of the addiction to the immediate effects of nicotine and, thereafter, reduce the amount of nicotine in order to wean the patient completely off of the addiction to nicotine, thereby allowing the patient to break their nicotine addiction.

An aspect of this invention is that it allows for the formation of nicotine particles in different sizes designed for delivery to different areas of a patient's lungs.

An aspect of the invention is that it allows the patient to be weaned off of (1) the need for immediate nicotine delivery as obtained when smoking, and (2) the need for nicotine at all.

These and other aspects, objects, advantages, and features of the invention will become apparent to those skilled in the art upon reading this disclosure.

BRIEF DESCRIPTION OF THE DRAWINGS

FIG. 4 summarizes the modified Fagerström test for evaluating intensity of physical dependence on nicotine. Adapted with permission from Heatherton T F, Kozlowski L T, Frecker R C, Fagerström K O. The Fagerström test for nicotine dependence: a revision of the Fagerström Tolerance Questionnaire. Br J Addict 1991; 86:1119-27.

DEFINITIONS

Figure 1:
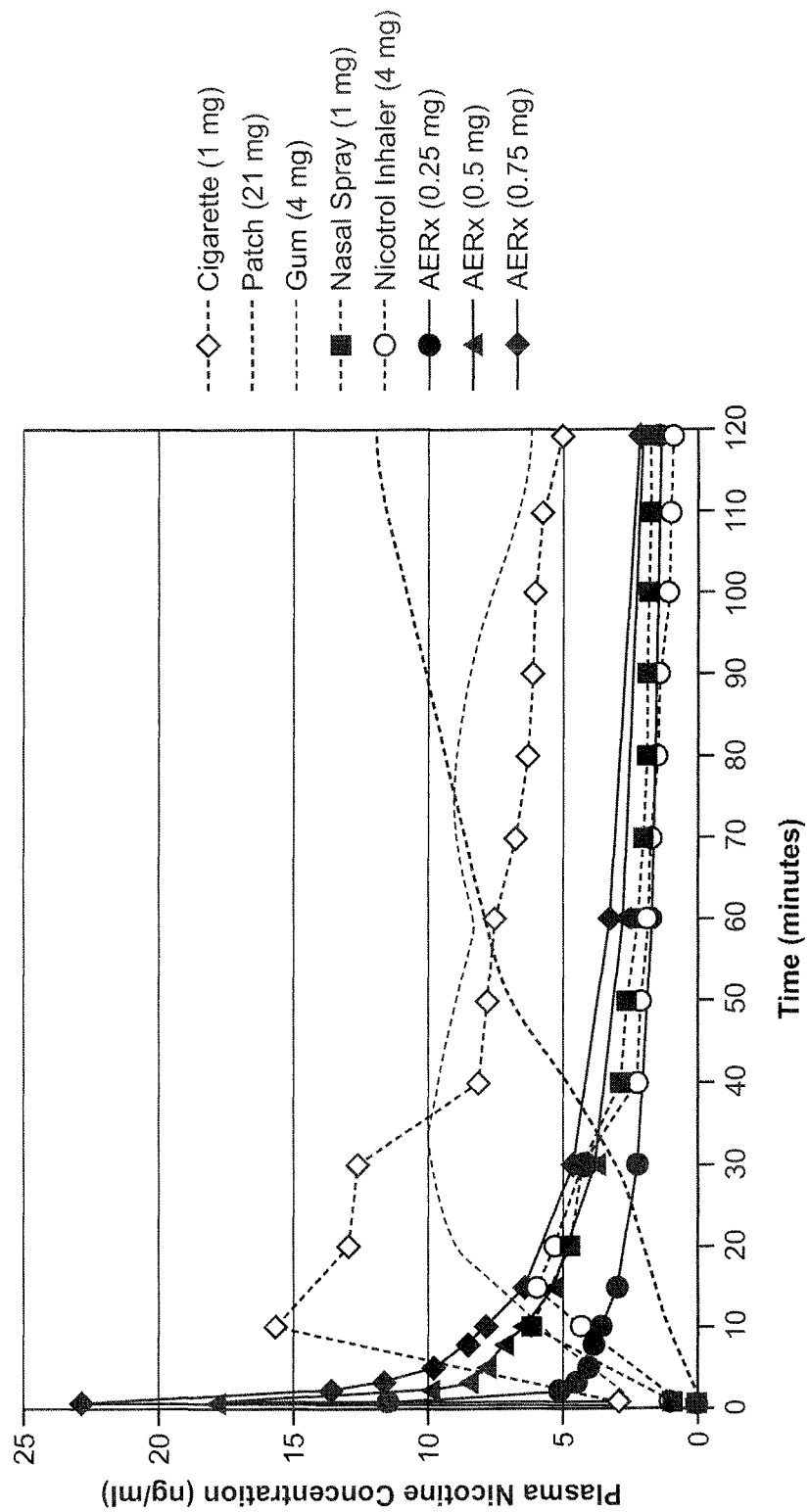
FIG. 1 compares the arterial nicotine profiles produced for cigarettes and various nicotine replacement therapies. The data is adapted from Rigotta, N. A., NEJM vol. 346, No. 7, (February 2002).

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); The Glossary of Genetics, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

An "antidepressant" refers to a substance that is used in the treatment of mood disorders, as characterized by various manic or depressive affects.

The term "anxiolytic" refers to any compound that has the effect of relieving anxiety.

A "bioadhesive component" is one which aids the compound containing it in associating with biological tissue.

The term "nicotine" is intended to mean the naturally occurring alkaloid known as nicotine, having the chemical name S-3-(1-methyl-2-pyrrolidinyl)pyridine, which may be isolated and purified from nature or synthetically produced in any manner. This term is also intended to encompass the commonly occurring salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate, camphorate and pamoate salts. Nicotine is a colorless to pale yellow, strongly alkaline, oily, volatile, hygroscopic liquid having a molecular weight of 162.23 and the formula:

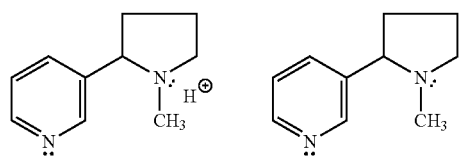

Structure and ionization of nicotine. Nicotine is approximately 10% of the particulate weight in cigarette smoke. Brand differences change this percentage. It is monoprotonated at most physiological pH values. The diprotonated ion would exist at pH values found in the stomach. Metabolism is largely due to oxidation. Cotinine is a major metabolite; however, there are at least 4 primary metabolites of nicotine and all are encompassed by the use of this term herein.

The term "form of nicotine" further includes any pharmacologically acceptable derivative, metabolite or analog of nicotine which exhibits pharmacotherapeutic properties similar to nicotine. Such derivatives and metabolites are known in the art, and include cotinine, norcotinine, nornicotine, nicotine N-oxide, cotinine N-oxide, 3-hydroxycotinine and 5-hydroxycotinine or pharmaceutically acceptable salts thereof. A number of useful derivatives of nicotine are disclosed within the Physician's Desk Reference (most recent edition) as well as Harrison's Principles of Internal Medicine. In addition, applicants refer to U.S. Pat. Nos. 5,776,957; 4,965,074; 5,278,176; 5,276,043; 5,227,391; 5,214,060; 5,242,934; 5,223,497; 5,278,045; 5,232,933; 5,138,062; 4,966,916; 4,442,292; 4,321,387; 5,069,094; 5,721,257; all of which are incorporated herein by reference to disclose and describe nicotine derivatives and formulations.

"Free base nicotine" refers to the form of nicotine that predominates at high pH levels. Free base nicotine is particularly potent and more addictive than nicotine salts which display a lower affinity to nicotinic receptors.

"A pharmaceutically active nicotine formulation" is a formulation having at least one form of nicotine as a component, and may include additional additives and drug dosages.

The physiologically active form of nicotine is the S-(−)-isomer. Certain compounds of the present invention may exist in particular geometric or stereoisomeric forms. The present invention contemplates all such compounds, including cis and trans isomers, R and S enantiomers, diastereomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The term "dual-release" is used herein to refer to a formulation comprised of two components, one which releases nicotine or a nicotine derivative or nicotine substitute immediately, and one component which releases nicotine or a nicotine derivative or nicotine substitute over a prolonged period of time.

The term "diameter" is used herein to refer to particle size as given in the "aerodynamic" size of the particle. The aerodynamic diameter is a measurement of a particle of unit density that has the same terminal sedimentation velocity in air under normal atmospheric conditions as the particle in question. In connection with the present invention, it is important that particles, on average, have the desired diameter so that the particles can be inhaled and targeted to a specific area of the lungs. For example, to target the alveolar ducts and alveoli for oral inhalation at moderate to high inspiratory flow rates, the particles should have a diameter in a range of about 0.5 μm to about 2 μm.

The term "porous membrane" shall be interpreted to mean a membrane of material in the shape of a sheet having any given outer perimeter shape, but preferably covering a package opening which is in the form of an elongated rectangle, wherein the sheet has a plurality of openings therein, which openings may be placed in a regular or irregular pattern, and which openings have a diameter in the range of 0.25 µm to 4 µm and a pore density in the range of $1 \times 10^4$ to about $1 \times 10^8$ pores per square centimeter. The membrane functions to form an aerosolized mist when the formulation is forced through it. Those skilled in the art may contemplate other materials which achieve this function as such materials are intended to be encompassed by this invention.

The terms "treatment", "treating", and the like are used interchangeably herein to generally mean obtaining a desired pharmacological and/or physiological effect. The terms are used in a manner somewhat differently than the terms are typically used in that what is intended by the method of treatment of the invention is to allow a patient to overcome an addiction to nicotine and thereby allow the patient to quit smoking. The treating effect of the invention provides a psychological effect in that the invention originally delivers high doses of nicotine in a manner that simulates the nicotine delivery obtained from a cigarette. The patient then becomes accustomed to relying on the methodology of the invention to provide an immediate "rush" of nicotine. Eventually, the treatment of the invention reduces the amount of nicotine so as to allow the patient to completely "wean" off of nicotine and to quit smoking.

All publications mentioned herein are incorporated herein by reference to described and disclose specific information for which the reference was cited in connection with. The publications discussed herein are provided solely for their stated disclosure prior to the filing date of the present application. Nothing herein is to be construed as an admission that the invention is not entitled to antedate such publications by virtue of prior invention. Further, the actual publication date may be different from that stated on the publication and as such may require independent verification of the actual publication dates.

DETAILED DESCRIPTION OF EXEMPLARY EMBODIMENTS OF THE INVENTION

I. Introduction

The present invention provides systems and methods for supplying nicotine therapy to a patient. Certain formulations used in the systems of the invention contain at least two forms of nicotine that in combination mimic the pharmacological delivery of nicotine produced by smoking a cigarette. In a single puff, the invention provides a nicotine dosage that rapidly peaks, mirroring the peak arterial concentration produced by smoking tobacco (FIG. 1). Thus the present invention provides a method wherein the patient obtains an influx of nicotine into the circulatory system at a rate which substantially matches the rate which nicotine would enter the circulatory system when smoking. This is obtained because, at least at first, the invention provides sufficiently small particles such that they are inhaled deeply into the lung, i.e. 50% or more of the particles are inhaled deeply into the lung and thereby quickly enter the patient's circulatory system.

The present invention is also advantageous in that the rate at which the delivered nicotine enters the circulatory system can be gradually decreased by gradually increasing the size of the aerosolized particles delivered to the patient. This can be done over any desired period of time and in any desired number of phases. Changes in the size of aerosolized particles may be through milling of the powder nicotine formulations provided, or by modification of the delivery device(s) of the invention. For example, a finer aerosol may be formed from a liquid nicotine formulation of the invention by rapidly passing the liquid through a porous membrane having pores with a smaller diameter.

Lastly, the invention provides a means whereby the amount of nicotine delivered to the patient's lung can be gradually varied in a number of different ways. Firstly, it can be increased or decreased by increasing/decreasing the concentration of nicotine in the aerosolized formulation. Secondly, it can be varied by merely changing the number of administrations of aerosolized doses. Thirdly, it can be varied by changing the size of the dose aerosolized and inhaled by the patient. The amount delivered to the lung will affect the rate of absorption and therefore the time and magnitude of the nicotine peak. The rate of absorption can be also varied by changing the pH of formulation. Lastly, all or any number of these parameters can be changed from one group of packages to the next, and therefore be engineered such that a gradual reduction in the peak plasma levels of nicotine is achieved.

As depicted in FIG. 1, current nicotine therapies are characterized by slow absorption and low blood levels of nicotine, limiting their utility. The present invention replaces the nicotine that a smoker receives from smoking a cigarette by providing a rapid pulse of bioavailable nicotine to the smoker on demand that may be optionally followed by a slow release of nicotine which provides a prolonged circulating concentration of nicotine when a second, slower releasing form of nicotine is also used. More specifically, the present invention provides a treatment methodology wherein a patient's initial arterial nicotine plasma concentration over a selected time, i.e., the arterial nicotine plasma concentration-rate profile, substantially correlates to that of the patient when smoking a cigarette.

One treatment methodology of the present invention creates an aerosol of nicotine particles. The nicotine particles may be formed from any liquid containing nicotine including a solution, or suspension of nicotine, or a dry powder formulation, and aerosolized in any known manner including (1) moving the formulation through a porous membrane in order to create particles or (2) a dry powder where the particles of powder have been designed to have a desired diameter and the dry powder formulation is dispersed using external sources of energy such as compressed air, or the patient's own breathing. Increasing the size of the particles from about 1-2 micrometers upwards causes the particles to be deposited higher in the respiratory tract. Higher regions of the respiratory tract have less tissue surface area than lower regions. As the overall rate of absorption is directly proportional to the surface area of the tissue on which the particles are deposited, nicotine is absorbed more slowly through the mucosal membranes of the upper respiratory tract. Thus the effect of increasing particle size is to deposit the inhaled particles in a higher region of the respiratory tract with a concomitant reduced absorption from the lung over time and a more sustained release of the drug. Thus one method of practicing the present invention is to provide a formulation comprising two forms of nicotine, one that produces fine particles of small diameter and another that produced larger particles. The larger particles deposit in the upper respiratory tract providing low level sustained drug release, while the smaller particles penetrate to the deep lung providing a rapid pulse of available nicotine similar to that provided by a cigarette.

Another treatment methodology of the present invention is to create a liquid or liquid suspension containing two different forms of nicotine or nicotine derivatives, one for rapid release and one for slow or delayed release. Some alternatives to this embodiment of the invention include the administration of the first nicotine form in a manner providing a rapid pulse of available nicotine to the users bloodstream. This may be accomplished by inhalation of the first form. The second form of nicotine may then be administered in an alternative manner, such as buccally in a tablet, capsule, caplet, lozenge, troche, gelcap, quick dissolve strip; transdermally such as via a patch or cream; or intranasally.

The method of the invention has applicability to smokers wishing to quit or trying to quit who have experienced all or any of the nicotine withdrawal symptoms associated with smoking cessation, such as craving for nicotine, irritability, frustration or anger, anxiety, drowsiness, sleep disturbances, impaired concentration, nervousness, restlessness, decreased heart rate, increased appetite and weight gain.

While particularly applicable to smoking cessation, pulmonary, oral, or parenteral administration of nicotine could be of value for the treatment of other diseases, such as for patients suffering from neurodegenerative diseases, psychiatric disorders and other central nervous system disorders responsive to nicotinic receptor modulation (see U.S. Pat. Nos. 5,187,169; 5,227,391; 5,272,155; 5,276,043; 5,278,176; 5,691,365; 5,885,998; 5,889,029; 5,914,328). Such diseases include, but are not limited to, senile dementia of the Alzheimer's type, Parkinson's disease, schizophrenia, obsessive-compulsive behavior, Tourette's Syndrome, depression, attention deficit disorder, myasthenia gravis and drug addiction. These embodiments and others are discussed in greater detail, below.

II. Tobacco-Less Formulations

Tobacco-less formulations of the present invention are preferably suitable for formation of aerosols. Certain formulations of the invention contain at least two forms of nicotine. Preferable embodiments are powders, semisolids, liquids, semiliquids and suspensions (e.g., suspensions of liposomes). The formulations may optionally include other drugs, excipients, permeation enhancers, preservatives, absorption enhancers, binding agents, buffers, and the like that enhance the efficacy or ease the use of the claimed invention. Typical nicotine forms of the invention include nicotine dissolved in water or dry powder nicotine with a carrier used to adjust the pH to the desired range. Methods of formulating liquids and liquid inhalers are disclosed in U.S. Pat. Nos. 5,364,838; 5,709,202; 5,497,763; 5,544,646; 5,718,222; 5,660,166; 5,823,178; and 5,910,301; all of which are incorporated by reference to describe and disclose such. Contemplated components of the claimed invention are discussed in greater detail, below.

A. Suitable Forms of Nicotine

Formulations of the present invention are tailored to provide a rapid increase of arterial nicotine concentration. Preferably this rapid increase in arterial nicotine concentration mimics that produced when smoking a cigarette. To this end, certain nicotine formulations of the invention include two forms of nicotine that in combination more closely mimic the pharmacological profile of nicotine delivery of a cigarette. The nicotine forms of the invention may be powders, emulsions, semi-solids, semi-liquids, suspension, liquids, or encapsulated. Preferably the nicotine forms are suitable for formation of aerosols that are amenable to inhalation. Some embodiments of the invention include two forms of nicotine. When a formulation containing two forms of nicotine is inhaled, the first form of nicotine has a smaller particle diameter than the second form of nicotine. This allows the first form of nicotine to be deposited in the deep lung where it is rapidly transferred to the user's blood stream and reaches the users central nervous system within 5 minutes, preferably in less than 4, 3, 2 or 1 minute. The larger particle size of the second form of nicotine results in deposition of this nicotine form higher up in the respiratory tract. As a result, the second form of nicotine is released more slowly to the users circulatory system with a more sustained effect. Nicotine forms of the invention are discussed in greater detail, below.

1. First Form of Nicotine

The first form of nicotine is preferentially inhaled as this method of administration provides the most rapid delivery without resorting to invasive techniques such as injection. Inhalation allows for a suitable first form of nicotine arterial concentration in the patient within 5 minutes of delivery. Typically this arterial concentration is at least 10, 12, 14 or 15 ng/ml, and this concentration is achieved within 5, preferably within 4, 3, 2, or 1 minute or less from inhalation of the claimed formulation.

To facilitate the rapid delivery of the drug to the users central nervous system when inhaled, the particle or droplet size of the first form of nicotine is controlled and kept small in order to allow the particles to reach the deep lung. Typically this size is between about 1 μm and about 4 μm in diameter, more preferably about 2 or 3 μm.

The first form of nicotine may have a fluid component having a basic pH, preferably having a pH of more than 7.5, 8.0, or 8.5. A basic pH facilitates formation of the more potent free base form of nicotine, which is a more potent form than nicotine salts. As discussed below, the nicotine forms of the claimed formulation may be encapsulated for example in microspheres. Encapsulation allows the nicotine forms of the formulation to be segregated and therefore they may be delivered with different additives, including buffers adjusting pH, due to their respective microenvironments.

2. Second Form of Nicotine

The second form of nicotine in the formulations of the invention are present in an amount to maintain a second form of nicotine arterial concentration in the patient for at least 60 minutes after delivery. This second form of nicotine arterial concentration is generally lower than the first form of nicotine arterial concentration, typically being at least about 8 ng/ml, preferably about 6 ng/ml, more preferably at least about 5 ng/ml, or at least about 4, 3, 2 ng/ml.

Delivery of the second form of nicotine may be performed using any suitable method with preferable methods being buccally (e.g., as a gum, quick dissolve strip, or lozenge composition), transdermal patch, inhalation, or other method that allows for sustained release of the second form of nicotine over a period of several minutes to hours, preferably at least 30, 40, or 60 minutes, more preferably 90 or 120 minutes. The second form of nicotine may be delivered at any pH, but is more preferably delivered as a salt at neutral or acidic pH, e.g., within a pH range of 7 to 3. Acidic pH values are particularly preferred, e.g. pH 5, 4 or 3.

A preferred method of administering the formulations of the invention is through inhalation. When inhaled, the second form of nicotine generally has a larger particle size than the first form of nicotine. As discussed elsewhere in this specification, the larger particle size results in the second form of nicotine being deposited preferentially in the upper respiratory tract rather than the deep lung. Deposition in the higher respiratory airways results in the second form of nicotine reaching the blood system and the receptors of the patient's central nervous system more slowly than is the case for the first form of nicotine deposited in the deep lung. This aids in the sustained release of lower levels of second form of nicotine to the blood as desired in mimicking the pharmacological administration of nicotine via a cigarette. Thus particles or droplets of the formulation containing the second form of nicotine are preferably in the range between about 4 μm and about 12 μm, more preferably between about 5 μm and about 10 μm, preferentially between about 6 μm and about 8 μm in diameter, as these sizes facilitate deposition of the particles or droplets in the upper airway passages of the lung.

To further aid in the sustained release of the second form of nicotine, this component of the formulation may optionally include a slow release component such as cyclodextrin. The second form of nicotine may also be encapsulated using any of the methodologies well known to those of skill in the art including packaging within microspheres. Encapsulation in microspheres has the added advantage of facilitating delivery of the first and second forms of nicotine at different pH values. For example, the first form of nicotine may be delivered in free base form having a basic pH whereas the second form of nicotine is delivered in salt form as an acidic pH. As is known, the free base form interacts with the nicotinic receptor eliciting a larger response than more basic forms of the drug.

Preferred microspheres for use in the invention include polyglycolide microspheres. Microspheres may also optionally include a bioadhesive component such as hyaluronic acid.

Microspheres and liposomes of the present invention may be constructed using techniques well-known to those of skill in the art. For example, liposomes containing the second form of nicotine of the present invention may be prepared, for example, by suspending a thin layer of purified phospholipids in a solution containing the second form of nicotine and then treating the suspension in a conventional manner such as ultrasonication. A "Liposome" is a closed vesicle of lipid bilayer encapsulating an aqueous compartment therein. It is known that the lipid bilayer membrane structure is extremely similar to biological membranes.

3. Supplemental Drugs

In addition to the nicotine forms discussed above, the tobacco-less compositions of the present invention may optionally include supplemental pharmaceutically-active components. These supplemental components may aid in delivery of the nicotine forms of the formulation, treat diseases, or make the formulations of the invention more acceptable to the patient-user.

Particularly preferred supplemental drugs include antidepressants and anxiolytics such as selective serotonin reuptake inhibitors, e.g., citalopram, escitalopram, fluoxetine, paroxetine, sertraline, and the like. Serotonin and norepinephrine reuptake inhibitors are also preferred, such as duloxetine, venlafaxine, and the like. Norepinephrine and dopamine reuptake inhibitors such as bupropion may also be used. Tetracyclic antidepressants such as mirtazapine; combined reuptake inhibitors and receptor blockers such as trazodone, nefazodone, maprotiline; tricyclic antidepressants, such as amitriptyline, amoxapine, desipramine, doxepin, imipramine, nortriptyline, protriptyline and trimipramine; monoamine oxidase inhibitors, such as phenelzine, tranylcypromine, isocarboxazid, selegiline; benzodiazepines such as lorazepam, clonazepam, alprazolam, and diazepam; serotonin 1A receptor agonists such as buspirone, aripiprazole, quetiapine, tandospirone and bifeprunox; and a beta-adrenergic receptor blocker, such as propranolol, may also be added to enhance the claimed tobacco-less formulations of the present invention.

Supplemental drugs may be delivered concomitantly with the formulations of the present invention, or may be administered independently. Supplemental drug delivery may be via any suitable method known in the art including orally, inhalation, injection, etc.

B. Pharmaceutically Acceptable Excipients

The formulations of the present invention are administered to a human and may contain one or more pharmaceutically-acceptable excipients, or carriers. Suitable excipients and their formulations are described in Remington's Pharmaceutical Sciences, 16th ed., 1980, Mack Publishing Co., edited by Oslo et al. Typically, an appropriate amount of a pharmaceutically-acceptable salt is used in the formulation to render the formulation isotonic. Examples of the pharmaceutically-acceptable excipients include liquids such as saline, Ringer's solution and dextrose solution. The pH of the solution is preferably from about 3 to about 8, and more preferably from about 3 to about 7, although the pH may be varied according to the drug cocktail. The formulation may also comprise a lyophilized powder or other optional excipients suitable to the present invention including sustained release preparations such as semipermeable matrices of solid hydrophobic polymers, which matrices are in the form of shaped articles, e.g., films, liposomes or microparticles as discussed above. It will be apparent to those persons skilled in the art that certain excipients may be more preferable depending upon, for instance, the route of administration the concentration of the nicotine formulation being administered.

Optional Additives

The medicaments of the present invention may optionally include other pharmacologic agents used to treat the conditions listed above, such as UTP, amiloride, antibiotics, bronchodilators, anti-inflammatory agents, and mucolytics (e.g. n-acetyl-cysteine). In addition to including other therapeutic agents in the medicament itself, the medicaments of the present invention may also be administered sequentially or concurrently with the one or more other pharmacologic agents. The amounts of medicament and pharmacologic agent depend, for example, on what type of pharmacologic agent(s) are used, and the scheduling and routes of administration.

C. Propellants

Tobacco-less formulations of the present invention may also include a propellant suitable for aerosolizing the pharmaceutically active nicotine formulation. Suitable propellants are well-known in the art and include compressed air, nitrogen, hydrofluoroalkanes (HFAs) and the like. An important aspect of any propellant used in the present invention is that it not react with nicotine or other pharmaceutically-active components of the tobacco-less formulations of the claimed invention.

III. Methodology

The penetration of aerosolized nicotine particles into the respiratory tract is determined largely by the size distribution of the particles formed and the way the patients breath just before, during and just after the administration of the medicament by inhalation. Larger particles, i.e., particles with a diameter greater than or equal to 5 μm, deposit predominantly on the upper airways of the lungs (see FIG. 1). At normal breathing rates, particles having a diameter in a range of about >2 microns (μ) to <5 microns (μm) deposit predominantly in the central airways. Smaller particles having a diameter <2 microns (μm) penetrate to the peripheral region of the lungs if they are delivered early in the breath at a low inhalation rate and the subject. As observed with cigarette smoke, breath-holding enhances the deposition of very small particles in the respiratory tract.

In one aspect of the invention the treatment methodology begins with particles of a given size, carries out treatment for a given period of time after which the particles are increased in size. The particles initially administered to the patient penetrate deeply into the lung, i.e., the smallest particles (e.g., 0.5 to 2 microns (μ)) target the alveolar ducts and the alveoli. When the deepest part of the lung is targeted with the smallest particles the patient receives an immediate "rush" from the nicotine delivered which closely matches that received when smoking a cigarette. These small particles can be obtained by milling powder into the desired size and inhaling the powder or by creating a solution or suspension and aerosolizing the formulation, e.g. by nebulization or by moving the solution or suspension through the pores of a membrane. In either case, the desired result is to obtain particles which have a diameter in the range of 0.5 μm to about 2 μm. Those skilled in the art will understand that some of the particles will fall above and below the desired range. However, if the majority of the particles (50% or more) fall within the desired range then the desired area of the lung will be predominantly targeted.

In practicing the present invention, the patient is allowed to take a single inhalation of the tobacco-less formulation of the invention when a cigarette is desired. For example, the patient would be instructed to inhale the tobacco-less formulation when the patient would normally smoke a cigarette. In this manner, the patient will become accustomed to finding that the device administers nicotine into the patient in a manner similar to a cigarette. In one embodiment of the invention the concentration of the nicotine in the tobacco-less formulation could be reduced gradually over time. This could be done over a sufficiently long period of time so as to allow the patient to wean off of nicotine. However, in another embodiment of the invention the amount of nicotine is kept substantially constant but the size of the aerosolized particles created are increased.

In another treatment methodology, the patient would begin the treatment with a low dose of the tobacco-less formulation of the invention and this dosage would gradually be raised as the patient grew more tolerant of the formulation. While increasing the tobacco-less formulation dosage to the most effective dose for that particular patient, the patient would gradually cease smoking until the tobacco-less formulation completely replaced the cigarette. Once the cigarette habit is broken, the patient would gradually lower the dosage of the tobacco-less formulation until the nicotine addiction was broken.

Another treatment methodology would gradually increase the size of the particles for the first form of nicotine. The increased particle size targets predominantly the respiratory tract above the alveolar ducts and below the small bronchi. This can generally be accomplished by creating aerosolized particles of nicotine which have a size and range of about 2 μm to about 4 μm. Administration is carried out in the same manner as described above. Specifically, the patient administers the aerosolized nicotine when nicotine cravings are experienced. Since the patient has become adjusted to receiving the nicotine "rush" from the smaller sized particles, the patient will expect and is therefore likely to experience the same "rush" when administering the slightly larger particles. However, the effect will be less immediate, or less intensive depending the magnitude and timing of the peak, as a consequence of the particles being deposited predominantly in a higher region of the respiratory tract. This procedure is carried out over a period of time, e.g., days or weeks. In one embodiment of the invention it is possible to reduce the dose of aerosolized nicotine delivered to the patient during this second phase. However, the dose may remain constant.

The treatment can be completed after any phase, e.g. after the second phase. However, in accordance with a more preferred embodiment of the invention a third phase of treatment is carried out. Within the third phase the particle size of the first form of nicotine is increased again. The particles are increased to a size in a range from about 4 μm to about 8 μm or, alternatively, perhaps as large as 12 μm. These larger particles will target predominantly the upper airways. The larger particles will give a very small immediate "rush" but will still be absorbed through the mucous membranes of the patient's respiratory tract. Accordingly, the patient will be administering nicotine doses which may be the same as those doses administered at the beginning of treatment. At this point the treatment can take a number of different directions. The patient can attempt to stop administration by immediate and complete cessation of nicotine delivery. Alternatively, the patient can try to wean off of nicotine by delivering fewer doses during a given time period, or by decreasing the dose per use, as discussed below.

In another alternative, the same size dose (volume of aerosol formulation) is administered and delivered, creating the same amount of aerosol, but wherein the aerosolized particles contain progressively less nicotine (i.e., more dilute concentration). The amount of nicotine can be decreased until the patient is receiving little or no nicotine. Those skilled in the art reading this disclosure will recognize variations on the overall method and methods for stopping treatment.

In yet another alternative embodiment the amount of nicotine, concentration of nicotine and particle sizes created by the formulation are all maintained the same from one group of packets to the next. However, the pH of the formulation within the packets from one group to the next is changed and is generally changed from a high or basic pH to a low or acidic pH. Thus, for example, the pH of the packets within a first group could be at 9.0 and the pH of the formulation in a second group of packets could be 8.0, followed by a third group at 7.0 followed by a fourth group at 6.0 followed by a fifth group at 5.0. Those skilled in the art, reading this disclosure will understand that the variation in pH from one group to the next can be in any amount and the pH can begin and end at any point provided the resulting formulation does not cause damage to the lungs of the patient to an unacceptable degree. In preferred embodiments, the pH of the first form of nicotine is varied from basic to acid thereby gradually decreasing the amount of free base nicotine in the formulation. The pH of the second form of nicotine may also be adjusted, but preferably remains constant, typically at a neutral or acidic pH level.

In yet another embodiment of the invention the nicotine forms of the invention may include variations of all or any of the different parameters which include amount of nicotine, concentration of nicotine, particle size of aerosol created and pH of the formulation. Any one, two, three or four of the parameters can be varied from one administration to the next.

Methods of Administering Medicaments

The tobacco-less formulation described herein are intended to be administered by inhalation. Commercially available nebulizers for liquid formulations, including jet nebulizers and ultrasonic nebulizers may be useful for administration. Liquid formulations may be directly nebulized and lyophilized power nebulized after reconstitution. Alternatively the tobacco-less formulation may be aerosolized using a metered dose inhaler, or inhaled as a powder, for example lyophilized, spray-dried, freeze-dried or milled powder. In addition, a liquid medicament may be directly instilled in the nasotracheal or endotracheal tubes in intubated patients.

Effective dosages and schedules for administering the medicament may be determined empirically, and making such determinations is within the skill in the art Those skilled in the art will understand that the dosage of tobacco-less formulation of the invention that must be administered will vary depending on, for example, the person receiving the formulation, the route of administration, the particular type of formulation used and other drugs being administered to the patient. As previously noted, the formulation of the present invention may be administered in a single dose, or as multiple doses over time.

Supplemental Treatment Methodology

Smokers wishing to quit may be treated solely with respiratory nicotine as indicated above, i.e. by intrapulmonary delivery. However, it is possible to treat such patients with a combination of pulmonary administration and other means of administration, such as transdermal administration. Transdermal nicotine is preferably administered to maintain a steady state level of nicotine within the circulatory system. Nasal or buccal formulation could be used for nasal or buccal delivery which could supplement aerosolized delivery.

Based on the above, it will be understood by those skilled in the art that a plurality of different treatments and means of administration can be used to treat a single patient. For example, a patient can be simultaneously treated with nicotine by transdermal administration, nicotine via pulmonary administration, in accordance with the present invention, and nicotine which is administered to the mucosa.

IV. Nicotine Delivery Devices

The aspects of the invention described above such as changing the amount, concentration, or pH of the formulation or changing the particle size of the aerosol created with the formulation can be done independent of the delivery device. However, there are a number of features which can be included in the system which are specific to the device which delivers the formulation. For example, the device can be designed so as to avoid overdosing. This can be carried out by mechanically or electronically monitoring the number of doses a patient has delivered and locking out further use for a given time interval. Thus, this system can be used as a safety feature. In addition to a safety feature the device can be programmed in order to force the frequency of administration. This could be done in order to aid the patient in reducing the times the dose is delivered and thereby moving the patient forward towards a point in time when the patient no longer needs nicotine.

Any of the devices suitable for use with the invention could be designed to force the patient to use only a certain dosage form of the tobacco-less formulation for a given period of time and then require that the patient use another dosage form. In this way the device can be programmed to start the patient with, for example, a relatively high dose which can be quickly administered and thereafter allowing the device only to be activated when a second group with a smaller amount, lower concentration, etc. is used in the device.

The devices suitable for use with the invention can also be programmed to be patient and physician specific. Thus, the device can include a lock-out component which prevents the device being used except in the presence of another component which could, for example, be a wristband worn by the patient. The device could also be programmable only by a particular physician equipped with a device which sends a signal allowing the device to be reprogrammed.

Devices suitable for use with the invention can also be programmed to release larger or lesser amounts of formulation and fire the aerosol at different rates of speed. Either or both of these parameters can be changed by themselves, together or in combination with the other parameters relating to the formulation and particle size.

Precision delivery of small molecule drugs via the lung for systemic effect is possible. An electronic inhaler capable of delivering a liquid formulated drug stored in a unit dose packages has been described and disclosed in U.S. Pat. No. 5,718,222 entitled "Disposable Package for Use in Aerosolized Delivery of Drugs," and is incorporated herein by reference. A formulation of nicotine can be prepared for delivery with this system. Quantitative delivery of nicotine on demand provides a mechanism for nicotine replacement therapy which is unlikely to be associated with recidivism precipitated by the symptoms of physical withdrawal.

In one embodiment, the tobacco-less nicotine formulation of the invention is forced through the openings or pores of a porous membrane to create an aerosol. In a specific embodiment, the openings are all uniform in size and are positioned at uniform distances from each other. However, the openings can be varied in size and randomly placed on the membrane. If the size of the openings is varied, the size of the particles formed will also vary. In general, it is preferable to have the opening sizes within the range of about 0.25μ to about 6μ which will create particle sizes of about 0.5μ to 12μ which are preferred with respect to inhalation applications. When the openings have a pore size in the range of 0.25μ to 1μ they will produce an aerosol having particle sizes in the range of 0.5μ to 2μ, which is particularly useful for delivering nicotine to the alveolar ducts and alveoli. Pore sizes having a diameter of about 1μ to 2μ will produce particles having a diameter of about 2μ to 4μ, which are particularly useful for delivering nicotine to the area above the alveolar ducts and below the small bronchi. A pore size of 2μ to 4μ will create particles having a diameter of 4μ to 8μ, which will target predominantly the area of the respiratory tract from the small bronchi upward. It is well known to those of ordinary skill in the art that the relationship between particle size and the site of deposition is complex and depends on many additional factors but that all other things being equal, increasing the physical size of the particles above 1 micron upwards will cause shift of deposition in the respiratory tract from the deep lung towards the oropharyngeal cavity.

Increasing the size of the openings of the porous membranes produces nicotine formulation particles of increasing size. A strategy in which the blood levels of nicotine, and especially the peak levels, are reduced gradually will be the most effective in treating the symptoms of withdrawal, and thereby increase the chances of successful smoking cessation. In one embodiment of the invention, the size of the aerosolized nicotine particles is increased in a stepwise manner by using porous membranes that create "monodispersed" aerosols, wherein all the particles within the aerosol created have essentially the same particle size. Nicotine particles of increasing size are produced by using membranes of increasing pore sizes.

In another embodiment, the size of aerosolized tobacco-less nicotine formulation particles is increased in gradient fashion by using porous membranes that create "polydispersed" aerosols, wherein the particles within the aerosol created have different particle sizes. Membranes which have a broad range of pore sizes are used to produce nicotine particles of varying sizes.

As intrapulmonary administration is not 100% efficient, the amount of drug aerosolized will be greater than the amount that actually reaches the patient's circulation. For example, if the inhalation system used is only 50% efficient then the patient will aerosolize a dose which is twice that needed to raise the patient's nicotine level to the extent needed to obtain the desired results. More specifically, when attempting to administer 1 mg of nicotine with a delivery system known to be 50% efficient, the patient will aerosolize an amount of formulation containing about 2 mg of nicotine.

A device comprised of a container that includes an opening covered by a porous membrane, such as the device disclosed in U.S. Pat. No. 5,906,202, may be used to deliver nicotine. The device may be designed to have the shape and/or bear the markings of a pack of cigarettes, and may include the scent of tobacco. These features and others that address the behavioral component of cigarette smoking may enhance the effectiveness of the method described herein.

V. Dosing

Cigarettes contain 6 to 11 mg of nicotine, of which the smoker typically absorbs 1-3 mg; see Henningfield *N Engl J Med* 333:1196-1203 (1995). Factors influencing nicotine absorption include subject-dependent factors, such as smoking behavior, lung clearance rate, etc., morphological factors, and physiological factors, such as tidal volume, inspiratory and expiratory flow rate, particle size and density. See Darby et al., *Clin Pharmacokinet* 9:435-439 (1984). The systemic dose of nicotine per puff is extremely variable, however, peak plasma concentrations of 25 to 40 ng/mL of nicotine, achieved within 5 to 7 minutes by cigarette smoking, are believed typical. In accordance with the present invention, 0.05 mg to 10 mg, preferably 0.5 to 3 mg, and more preferably about 1 mg of nicotine are delivered to the lungs of the patient in a single dose to achieve peak blood plasma concentrations of 10 to 50 ng/mL. It is understood in the art that approximately twice the aerosolized dose must be delivered to the patient to achieve a given dose delivered to the lungs (lung dose). These specific amounts should not be relied on. Alternatively, the amounts should be measured, adjusted, re-measured and readjusted as needed to obtain the appropriate dosing. An aspect of the invention is to initially set out to deliver the nicotine preparation in a manner that satisfies the craving for high plasma levels of nicotine in the subject and then gradually changing the nature of the inhaled nicotine formulation in terms of the amount of nicotine, its concentration as well as site of deposition so as to gradually reduce the peak plasma nicotine levels to wean the subject off tobacco. The amount needed will vary based on many factors including how much the patient smokes, and the patient's age, sex, weight and condition.

The amount of nicotine administered will vary based on factors such as the age, weight and frequency of smoking or nicotine tolerance of the smoker. Other factors, such as daily stress patterns, and demographic factors may also help to determine the amount of nicotine sufficient to satisfy the smoker's craving for the drug. Administering nicotine using the methods of the present invention can involve the daily administration of anywhere from 0.05 mg to 200 mg of nicotine, but more preferably involves the administration of approximately 10 to 100 mg per day, but these amount ranges should not be relied on. Amounts should be determined as indicated above.

The delivery of a large, or bolus, dose of nicotine has been avoided due to concerns about toxicities associated with nicotine. The present invention includes systems for delivering a bolus dose of nicotine in a single inhalation with no dose-related acute serious side effects and a resultant decrease in acute nicotine cravings. The nicotine doses safely delivered approximate the equivalent of an entire cigarette (approximately 1 to 3 mg of nicotine).

Following an introductory period on a dose expected to be both tolerable and therapeutic for the individual patient, based on their smoking history, age, weight, overall health, etc., it is expected that the patient will titrate their dose up or down to the optimal dose required to adequately treat their acute cravings. The patient will remain at that dose until they have been able to break their addiction to tobacco products. Following that step, it is expected that patients would reduce their use of the inhaled nicotine formulation until they no longer require nicotine in any form.

It is anticipated that some patients will benefit from the concomitant use of antidepressants or anxiolytics to break their addiction to nicotine. These classes of drugs are likely to be particularly helpful during the final phase as the patient wean himself or herself off nicotine entirely. However, given the long run in time required for these therapeutics to achieve maximum efficacy it is anticipated that they may be prescribed throughout the entire course of treatment.

VI. Systems for Nicotine Therapy

The present invention also includes systems for delivery of the nicotine formulations described above. These systems typically include an inhaler that is capable of delivering a complete dose of the nicotine to the patient in a single puff or two puffs, or more. Nicotine dosages may be as high as that provided by smoking an entire cigarette or more, and may be modulated as described above according to the treatment provided. Systems of the present invention are also characterized as being used preferentially by smokers looking to break a smoking habit. Typical users of the present invention will have Fagerstrom scores between 4 and 10. The Fagerstrom test is well known in the art and is summarized in FIG. 4. Briefly, a patient is presented with a series of six questions that are scored based on the answer provided.

In its simplest embodiment, the invention is a system that delivers tobacco-less nicotine formulations. These formulations are delivered directly to the patient's circulatory system via the lungs. In this manner the nicotine formulation of the system provides a peak nicotine arterial concentration in the patient within 5 minutes of being inhaled by the patient.

In another embodiment, the invention includes a system having multiple groups of containers. Each container of each group contains a pharmaceutically active nicotine formulation that is substantially identical to that contained in every other container of the group, with the formulations in the respective groups of containers differing, as described in greater detail below. In some forms, the amount of nicotine formulation confined by the first group of containers is larger than the amount of nicotine formulation confined by the second group of containers. This may be necessary as the first group of containers is intended to provide a bolus of drug to the patient in a manner that provides a rapid increase in arterial nicotine concentration in a short period of time, typically less than five minutes.

The nicotine formulation in the first group of containers is functionally characterized as producing a peak in nicotine arterial concentration in a patient within 5 minutes of delivery. In order to provide this rapid onset of nicotine concentration, the formulation is delivered either directly to the circulatory system via inhalation. To facilitate delivery, the formulation is physically characterized as preferably being a powder or a liquid, and preferably is stored and delivered as a basic composition with a pH of greater than 7, preferably 7.5, 8, or 9. When in powder form, the formulation is finely milled with particles that contain nicotine having diameter typically between 1 μm and 5 μm. This facilitates delivery of the drug by inhalation into the airways and alveoli, typically in a single dose.

The nicotine formulation in each of the other group of containers is also substantially identical, but is physically, chemically or quantitatively different from the nicotine formulation confined by each other group of containers. Functionally, this second nicotine formulation differs from the first formulation as the second formulation is a slow-release form maintaining a second form of nicotine plasma concentration in the patient for at least 60 minutes after delivery. In order to maintain the nicotine concentration over a prolonged period, the second nicotine formulation is usually delivered in a slow release formula and/or in the form of a gum, crème, fast dissolve strip, transdermal patch, or other medium that either releases the drug over time or delivers the drug in a manner that is slower than that provided for the first nicotine formulation discussed above. The nicotine formulation contained in each group of containers is unique from all other groups of containers in the effective amount and rate of absorption of nicotine that it delivers to the lungs and from the lungs into the systemic circulation. These differences may be a result of changes to the nicotine formulation, such as concentration, particle size of powders, pH or any other parameter that would be obvious to those skilled in the art. In addition, the differences may be a result of variations that alter the efficiency of delivery of the formulation to the deep lung, such as membrane pore size or number, control of patient flow rate or any other parameter that would be obvious to those skilled in the art.

Still another aspect of the claimed invention is a system that has two groups of containers where each container of each group has at least one exit pore and confines substantially identical pharmaceutically active nicotine formulations, wherein the exit pore of each container of the first group is identical, the exit pore of each container of the second group is identical, and the exit pore of a first group container is different from the exit pore of a second group container.

In using the systems described above, the patient will typically take one dose of the nicotine. Alternatively, the patient may deliver the drug in incremental dosages. Multiple dosing may be provided to address the habitual puffing of a cigarette. In such circumstances the cumulative effect of incremental dosages is to deliver the same dose of nicotine as typically provided in one dosing event using the present invention. Dosing is discussed in greater detail, above.

VII. Assessing Addiction

A variety of methods may be utilized to assess the craving for nicotine, including but not limited to, the nicotine craving test specified by the Diagnostic and Statistical Manual of Mental Disorders, Revised Third Edition (DSM-III-R) (see (1991) J. Am. Med. Assoc. 266:3133); the Shiffman-Jarvik Craving Subscale (see O'Connell and Martin (1987) J. Consult. Clin. Psychol. 55:367-371 and Steur and Wewers (1989) ONF 16:193-198, also describing a parallel visual analog test); West et al. (1984) Br. J. Addiction 79:215-219; and Hughes et al. (1984) Psychopharmacology 83:82-87, each of which is expressly incorporated herein by reference.

A preferred nicotine craving scale is that specified in DSM-III-R, supra. According to this scale, a subject is asked to rate the severity of his craving for nicotine on a scale between 0 and 4, wherein 0 is none; 1 is slight; 2 is mild; 3 is moderate; and 4 is severe. Using the compositions and methods described herein, the subject should attain at least a one unit, and preferably at least a two unit, decrease in his craving for nicotine as measured by the protocol set forth in DSM-III-R from about 2 to 30 minutes after administration of the oral nicotine formulation. More preferably, the maximum reduction in craving for nicotine will occur from about 2 to 20 minutes, and more preferably from about 2 to 10 minutes after administration of the oral nicotine formulation.

The Shiffman-Jarvik Craving Scale is a six-item, forced-choice, self-report tool that measures cigarette craving. Each item has seven possible responses which correspond to scores ranging from 1 (no craving) to 7 (high craving). A mean score is obtained to determine the respondent's level of craving. A typical craving score measured 48 hours after the initiation of a smoking cessation program is between about 4 and 5; while a two-week follow-up craving scale will typically be between about 3 and 4. Using the compositions and methods described herein, the subject should attain at least a one unit, and preferably at least a two unit, decrease in his craving for nicotine as measured by the protocol set forth in the Shiffman-Jarvik Craving Scale from about 2 to 30 minutes after administration of the oral nicotine formulation. More preferably, the maximum reduction in craving for nicotine will occur from about 2 to 20 minutes, and more preferably from about 2 to 10 minutes after administration of the oral nicotine formulation.

The "craving questionnaire" craving scale employs a five item questionnaire that asks subjects to rate how much they had been missing their cigarettes, how difficult it had been to be without cigarettes, how much they had been aware of not smoking, how pre-occupied they had been with thinking about cigarettes, and how much they had craved their cigarettes. The subject responds to each question with a number between 1 and 3, where 1 is low and 3 is high. The ratings are combined to give a single craving score. According to this craving scale, a combined score of between about 9 and 12 is typical. Using the compositions and methods described herein, the subject should attain at least a three unit, and preferably at least a four unit, decrease in his craving for nicotine as measured by the protocol set forth for use with this craving questionnaire from about 2 to 30 minutes after administration of the oral nicotine formulation. More preferably, the maximum reduction in craving for nicotine will occur from about 2 to 20 minutes, and more preferably from about 2 to 10 minutes after administration of the oral nicotine formulation.

A subject's frequency of smoking can be quantified using an eight-question scale, termed the Fagerstrom Nicotine Tolerance Scale (see Fagerstrom (1978) Addict. Behav. 3:235-241 and Sachs (1986) Clinics in Geriatric Medicine 2:337-362) which provides a relative index of the degree of physical dependency that a patient has for nicotine. This test is shown in FIG. 4.

A similar smoking cessation program can be developed for the moderate smoker, i.e., those scoring 6 or less on the Fagerstrom test. For example, during the initial phase, a transdermal patch with a moderate loading of nicotine, typically in the range of about 10-40 mg, and preferably, about 25-30 mg, is administered in conjunction with the transmucosal administration of nicotine. The second phase of this smoking cessation program will consist of administration of a lower dosage transdermal patch, typically containing nicotine in the range of about 10-30 mg, and preferably, about 20-25 mg, optionally, with the transmucosal administration of nicotine, will be used for a period of from about 4 to 8 weeks. During the final phase or weaning period, either the patch or transmucosal administration will be used alone.

These tests have a variety of uses in practicing the instant invention. For example, the Fagerstrom test may be used to estimate nicotine tolerance and therefore the initial nicotine dose in treatment. Cravings scores may be used to determine the effectiveness of a given formulation dosage in suppressing the desire to smoke or chew tobacco.

As will be evident to one of skill in the art, the ability to measure the patient's arterial nicotine plasma levels can be of tremendous value in tailoring a smoking cessation or other therapy to the patient's needs. There has been very little discussion in the literature of using direct or indirect measurement of arterial nicotine levels as an integral part of smoking cessation therapy. The traditional interest in quantifying arterial nicotine levels has been related to research on efficacy of smoking cessation therapies. For example, research studies commonly used various measurement techniques to attempt to verify self-reports of smoking frequencies by study subjects. These include the measurement in saliva and blood plasma of nicotine, cotinine (the primary metabolite of nicotine), carboxyhemoglobin, and thiocyanate; and the measurement in expired air of carbon monoxide. The most frequently cited technique is the quantification of cotinine, a nicotine metabolite, in saliva. The quantification of cotinine in blood fluids can be accomplished by gas-liquid chromatography, radioimmunoas say, and liquid chromatography. (For a discussion of liquid chromatographic assays for cotinine, see Machacek and Jiang (1986) Clin. Chem. 32:979-982, herein incorporated by references.)

The present invention may optionally include the direct or indirect measurement of nicotine blood levels as an integral part of methods for treating conditions responsive to nicotine therapy, and particularly for smoking cessation therapy and for reducing nicotine craving. The nicotine blood levels can be measured before, during, or after the administration of the formulations of the invention, as an aid in determining the amount of nicotine to be administered and the frequency of administration. In a preferred embodiment, saliva samples are taken from the patients and used for measurement of cotinine, as a biochemical marker of nicotine blood plasma levels. Cotinine levels are determined using any of the analytical methods known to those skilled in the art. In a particularly preferred embodiment, the cotinine assay would be portable and easily and simply accomplished by the patient, as in an assay kit or strip indicator.

All publications and patent applications cited in this specification are herein incorporated by reference as if each individual publication or patent application were specifically and individually indicated to be incorporated by reference.

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

As can be appreciated from the disclosure provided above, the present invention has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results.

EXAMPLES

Example 1

Single-Dose Application of Deep Lung Nicotine Formulation

Smoking dependence appears partly related to the "high & fast" rise in plasma nicotine concentration achieved by cigarettes, cigars, and pipes. However, unlike cigarettes, current nicotine replacement therapies (NRTs) attain relatively "low & slow" nicotine plasma levels (FIG. 1). This example illustrates that a nicotine delivery system that provides cigarette-like plasma levels, serves to reduce acute craving, inhibit relapse, and result in higher smoking cessation rates compared with existing NRTs.

The AERx Essence System known in the art was used to deliver single-bolus doses of aerosolized nicotine to healthy adult male smokers. The AERx Essence is an all-mechanical, nonpropellant driven, hand-held device that uses individually packaged, single-use, dosage form strips. A uniformly fine, respirable aerosol is created when the drug solution is "extruded" through an array of submicron sized holes drilled into the dosage form strip. The fine aerosol that is generated allows the deep-lung deposition needed to achieve rapid and efficient absorption of drug similar to that obtained by smoking.

Methods

Eighteen healthy, adult male smokers were enrolled in a randomized, open-label, multiple-exposure study which was conducted in two parts. Two subjects were removed prior to Study Part 2 with sixteen subjects starting and completing Study Part 2. Subjects' ages ranged from 19-41 years (mean=27 years).

In Study Part 1, the tolerability and safety of seven nicotine concentrations were evaluated. In Study Part 2, subjects received one of three nicotine concentrations: 10, 20, or 30 mg/ml, delivering bolus nicotine lung doses of approximately 0.2, 0.4 and 0.7 mg, respectively. Measures of arterial nicotine plasma concentration and acute post-dosing cigarette craving scores (11-point VAS) were made following a single inhalation of nicotine.

Results

Safety and Tolerability:

No clinically significant changes in safety measures were noted following dosing (vital signs, ECG, spirometry, labs). A total of 119 adverse events (AEs) were recorded. Most AEs were reported as either mild or moderate and self-resolved without medication. No serious AEs were observed. The most commonly reported AEs were throat irritation, lightheadedness (Table 1).

TABLE 1

Incidence of most common Adverse Events (AE)

| Adverse Event (AE) | Incidence | Subjects Experiencing AE |
|---|---|---|
| Throat irritation | 46 | 17 |
| Lightheadedness | 22 | 11 |
| Cough | 20 | 10 |

Figure 2:
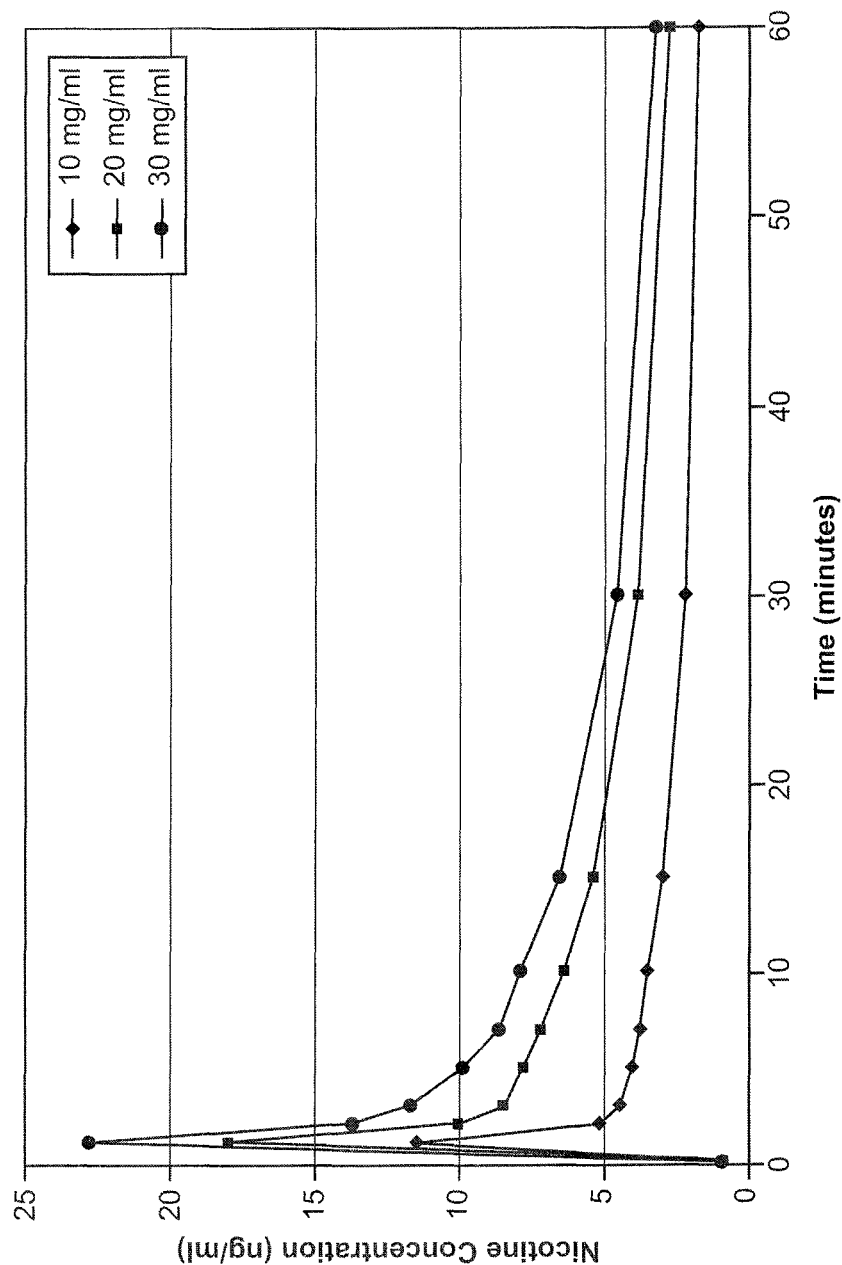
FIG. 2 depicts the mean arterial plasma nicotine concentrations for 16 human patients.

Pharmacokinetics:

Arterial plasma nicotine pharmacokinetics demonstrated rapid onset (Tmax=1 min) and substantial peak plasma concentrations. Maximum plasma concentrations (Cmax) and area under the concentration-time curves (AUC) were consistent with a trend toward dose proportionality (FIG. 2, Table 2).

TABLE 2

Mean Nicotine Pharmacokinetic Parameters

| Parameter | 10 mg/ml | 20 mg/ml | 30 mg/ml |
|---|---|---|---|
| Tmax (min) | 1 | 1 | 1 |
| Cmax (ng/ml) | 11.5 (9.5) | 18.0 (3.6) | 22.9 (9.0) |

TABLE 2-continued

Mean Nicotine Pharmacokinetic Parameters

| Parameter | 10 mg/ml | 20 mg/ml | 30 mg/ml |
|---|---|---|---|
| T½ (min$^{-1}$) | 136 (58) | 114 (18) | 97 (16) |
| AUC$_{0-t}$ (ng · min/ml) | 319 (219) | 532 (116) | 622 (218) |

Standard deviations are in parenthesis.

Standard deviations are in parenthesis.

Figure 3:
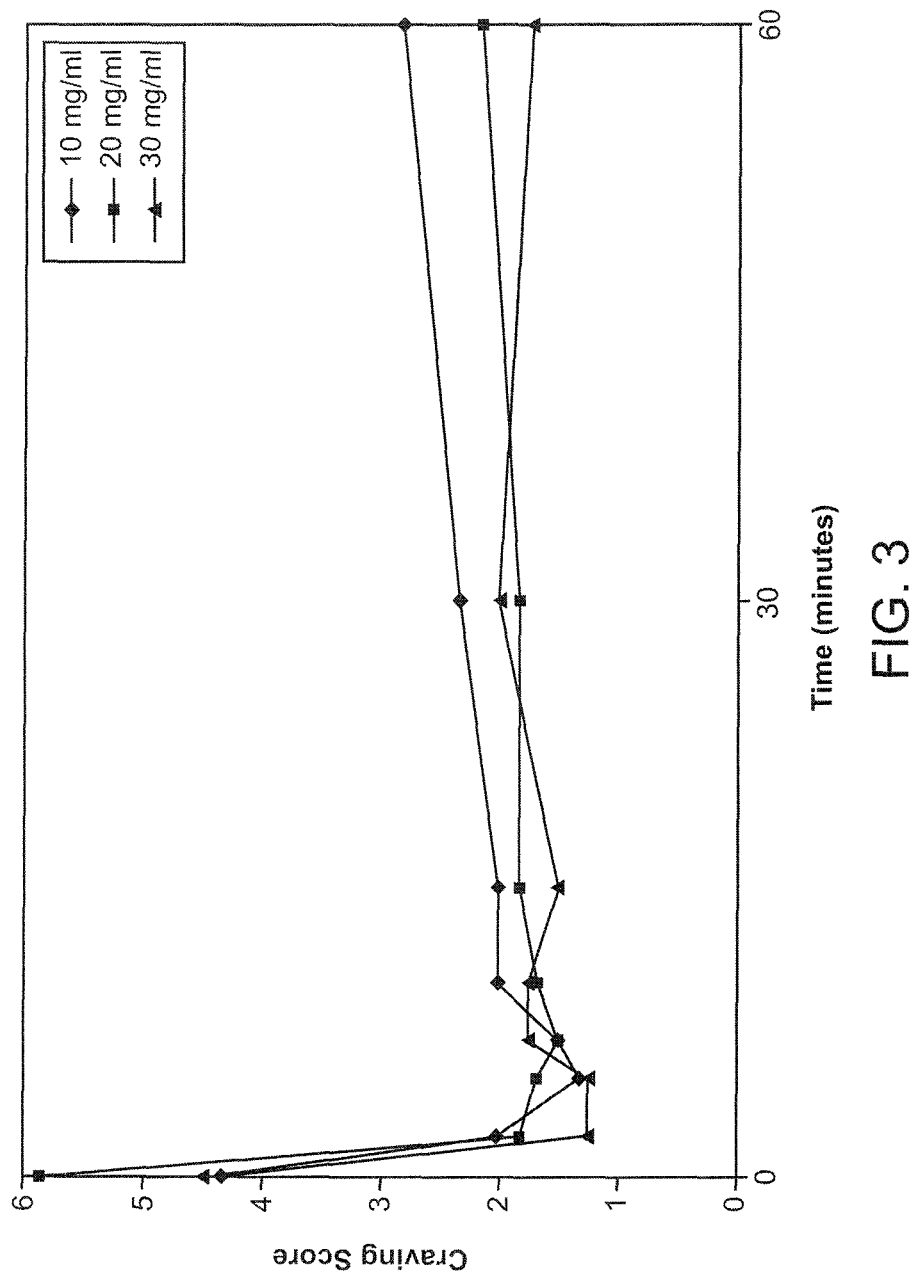
FIG. 3 depicts the mean craving scores for 16 human patients.

Acute Craving:

Patients were asked to rate their nicotine craving on a scale of 0 to 10 pre- and post-dosing. Nearly all subjects reported an acute reduction in craving or an absence of craving immediately following study dosing. A mean reduction in craving from baseline was observed following all three dose levels (FIG. 3). Combining all dose levels, mean craving declined from 4.9 to 1.4 within 5 minutes post-dosing, and remained below pre-dose baseline for the 4 hours of monitoring.

Conclusions

Inhaled nicotine via the AERx Essence appears safe and tolerable. The AERx Essence delivers inhaled nicotine with a PK profile that is consistent with the rapid delivery and absorption seen with cigarette smoking, and acute craving following inhaled nicotine via the AERx Essence appears to be acutely reduced Example 2

Use of Alternative Nicotine Forms

This example demonstrates the effectiveness of different nicotine dosage forms of the invention. The aim of the example is to illustrate that generically available nicotine formulations are suitable for use in the present invention.

Formulation studies were performed to evaluate the effectiveness of nicotine salts and pH on the stability of nicotine in AERx® dosage forms. Nicotine is a weak base (pka$_1$=3.4 and pKa$_2$=8.4) and in the un-ionized state had the capability to get absorbed into the polymeric materials used in many nicotine delivery systems. When a screening study was conducted in the pH 3.0-7.0 range using buffered nicotine sulphate and bitartrate, nicotine concentration was in effect unaltered for the two salts at the lower pH's of 3.0 and 4.0. Nicotine bitartrate was better in this pH range as compared to nicotine sulphate in terms of ensuring that there was no loss of nicotine into the polymeric dosage form materials. A theoretical calculation using the Henderson-Hasselbach equation indicated that the ratio of ionized to un-ionized species at pH 3.0 and pH 4.0 was 158489 and 15849, respectively, implying limited potential for absorption to occur at the lower pH of 3.0.

Aradigm's proprietary AERx® System was used in the present example. This system consists of the AERx® Strip™, a single-use disposable dosage form, and the AERx® device, which has two hand-held configurations: an electromechanical version and an all-mechanical version.

Nicotine formulations were packaged under aseptic conditions into the AERx® Strip, to create a sterile dosage form. Aerosol generation using the AERx® System is completed in one or two seconds via mechanical pressurization of the nicotine formulation. This pressurization causes the seal in the AERx® Strip between the drug reservoir and a nozzle array to peel open. This leads to the nicotine formulation being expelled through the nozzle array as a fine aerosol. By varying the size of the nozzle holes, the particle size of the aerosol can be modified to optimize regional lung deposition. The electromechanical AERx® system was modified to allow addition of dose titration capabilities into the system for this program.

Results

Analytical Assay Development for Nicotine Quantitation

A high performance liquid chromatography (HPLC)-based assay was developed in house to enable quantitation of nicotine (Table 3). The HPLC method was suitably modified for functional (aerosol) testing of AERx®-nicotine and a partial qualification conducted. The analytical performance parameters evaluated were: standard linearity, range, accuracy, precision, limit of quantitation (LOQ), system suitability, specificity and solution stability. The functional test method, in conjunction with the RP-HPLC method was qualified for use in determining emitted dose and particle size distribution of aerosolized nicotine. Nicotine working standard linearity, r2, was 1.000 and the linear concentration range was 0.5 to 40.0 µg/mL (Table 4).

TABLE 3

Analytical Method Parameters/Details
Reverse Phase High Performance Liquid
Chromatography (RP-HPLC) Method

| HPLC Column | Ace 5, C18 (25 cm × 4.6 mm, 5 µm) |
|---|---|
| Mobile Phase | 80% 20 mM Phosphate buffer, 20% Methanol, pH 5.0 |
| Wavelength (UV detector) | 259 nm |
| Flow Rate | 1.00 mL/min |
| Injection Volume | 20 µL |
| Column Temperature | 35° C. |
| Autosampler Temperature | Ambient |
| Run Time | 10 minutes |

TABLE 4

Summary of analytical results from method development

| Analytical Performance Parameters Evaluated | Results |
|---|---|
| Standard Linearity and Range | $R^2$ = 1.000, 0.5-40.0 µgmL |
| Accuracy and Precision | Passed acceptance criteria |
| Limit of Quantitation | 0.5 µg/mL |
| System Suitability and Specificity | Peak Area & RT: % RSD < 2%, Tailing Factor = 1.0, No interfering peak |
| Solution Stability | Standards Stability = 7 days, Diluent/Mobile Phase Stability = 15 days |

Nicotine Formulation Development

Selecting a Nicotine Salts:

After evaluation of availability of various grades of nicotine salts on the market, nicotine bitartrate and nicotine sulphate were selected for further screening. Both salts were purchased from Nicobrand Limited, Northern Ireland.

Formulation Concentrations:

A 0.9-1.0 mg lung dose was estimated as an efficacious upper end dose based on available literature. Estimating a 60% deep lung delivery efficiency for AERx®, the nicotine concentration chosen at the upper end was 32.0 mg/mL. Using the three step dose reduction strategy described above, the lower nicotine concentration was estimated to be 10.7 mg/mL. Initial formulation studies used a lower concentration of 8.0 mg/mL (prior to the finalization of a three-step dose reduction strategy), which was later finalized (using a three step dose reduction strategy) to be 10.7 mg/mL.

Formulation Stability in Pouches:

An initial formulation screening study was initiated utilizing nicotine formulations between the pH of 3.0-7.0 stored in pouches at 40° C./75% R.H. The pouches were made of the same polymeric material as the contact layer in AERx® dosage forms. In previous studies with a different but chemically similar drug, polymeric materials showed the potential for absorptive losses of drug from solution. Nicotine concentration as well as pH was monitored for a period of 28 days.

Results indicated no impact on pH over the 28 days period throughout the pH range evaluated (Tables 5 & 6). The concentration of nicotine decreased over time at higher pH values, consistent with the proposed absorption when in the unionized form (Tables 7 & 8). The concentration of nicotine was unaltered at pHs 3.0 and 4.0.

TABLE 5

Formulation stability- nicotine bitartrate pH results in pouches

| | Nicotine Bitartrate (controls) | | | | | | | | Nicotine Bitartrate (pouches) | | | | | | | |
|---|---|---|---|---|---|---|---|---|---|---|---|---|---|---|---|---|
| | 8 mg/mL | | | | 32 mg/mL | | | | 8 mg/mL | | | | 32 mg/mL | | | |
| Theoretical pH | T = 0 | T = 7 days | T = 15 days | T = 28 days | T = 0 | T = 7 days | T = 15 days | T = 28 days | T = 0 | T = 7 days | T = 15 days | T = 28 days | T = 0 | T = 7 days | T = 15 days | T = 28 days |
| 3.0 | 3.0 | 3.1 | 3.1 | 3.1 | 3.0 | 3.1 | 3.1 | 3.1 | 3.1 | 3.1 | 3.3 | 3.2 | 3.1 | 3.1 | 3.2 | 3.2 |
| 4.0 | 4.0 | 4.3 | 4.2 | 4.2 | 4.0 | 4.3 | 4.3 | 4.3 | 4.3 | 4.2 | 4.3 | 4.4 | 4.3 | 4.2 | 4.3 | 4.4 |
| 5.0 | 5.1 | 5.0 | 5.3 | 5.3 | 5.0 | 5.3 | 5.3 | 5.3 | 5.4 | 5.3 | 5.2 | 5.2 | 5.4 | 5.3 | 5.2 | 5.2 |
| 6.0 | 6.0 | 6.3 | 6.1 | 6.2 | 6.0 | 6.3 | 6.2 | 6.2 | 6.3 | 6.2 | 6.1 | 6.1 | 6.3 | 6.2 | 6.0 | 6.1 |
| 7.0 | 7.1 | 7.1 | 7.4 | 7.3 | 7.0 | 7.1 | 7.2 | 7.2 | 7.4 | 7.1 | 7.1 | 7.1 | 7.2 | 6.9 | 7.0 | 6.8 |

TABLE 6

Formulation stability- nicotine sulphate pH results in pouches

| | Nicotine Sulphate (controls) | | | | | | | | Nicotine Sulphate (pouches) | | | | | | | |
|---|---|---|---|---|---|---|---|---|---|---|---|---|---|---|---|---|
| | 8 mg/mL | | | | 32 mg/mL | | | | 8 mg/mL | | | | 32 mg/mL | | | |
| Theoretical pH | T = 0 | T = 7 days | T = 15 days | T = 28 days | T = 0 | T = 7 days | T = 15 days | T = 28 days | T = 0 | T = 7 days | T = 15 days | T = 28 days | T = 0 | T = 7 days | T = 15 days | T = 28 days |
| 3.0 | 3.0 | 2.7 | 2.8 | 2.8 | 3.0 | 2.7 | 2.8 | 2.8 | 2.9 | 2.7 | 2.8 | 2.8 | 2.8 | 2.8 | 2.9 | 2.8 |
| 4.0 | 4.0 | 4.1 | 4.1 | 4.1 | 4.1 | 4.0 | 4.0 | 4.1 | 4.1 | 4.0 | 4.1 | 4.1 | 4.0 | 4.0 | 4.1 | 4.1 |
| 5.0 | 5.0 | 5.1 | 5.1 | 5.1 | 5.1 | 5.1 | 5.1 | 5.1 | 5.2 | 5.1 | 5.0 | 5.1 | 5.2 | 5.1 | 5.0 | 5.0 |
| 6.0 | 6.0 | 6.2 | 6.1 | 6.1 | 6.0 | 6.2 | 6.1 | 6.1 | 6.2 | 6.1 | 6.0 | 6.1 | 6.2 | 6.0 | 5.9 | 6.0 |
| 7.0 | 7.0 | 7.3 | 7.1 | 7.1 | 7.0 | 7.2 | 7.1 | 7.1 | 7.1 | 6.9 | 6.9 | 6.9 | 7.1 | 6.9 | 6.9 | 6.8 |

TABLE 7

Formulation stability- nicotine bitartrate concentration results in pouches

| | Nicotine Bitartrate | | | | | | | |
|---|---|---|---|---|---|---|---|---|
| Formulation | % Recovery (8 mg/mL) | | | | % Recovery (32 mg/mL) | | | |
| Theoretical pH | T = 0 | T = 7 days | T = 15 days | T = 28 days | T = 0 | T = 7 days | T = 15 days | T = 28 days |
| 3.0 | 101.4 | 99.9 | 100.0 | 101.6 | 101.7 | 99.1 | 101.9 | 102.3 |
| 4.0 | 100.8 | 99 | 99.0 | 100.2 | 100.5 | 101.9 | 99.1 | 98.7 |
| 5.0 | 100.6 | 96.8 | 97.1 | 98.3 | 100.5 | 99.2 | 95.4 | 98.9 |
| 6.0 | 101.7 | 93.2 | 90.1 | 95.8 | 99.2 | 93.1 | 94.7 | 95.3 |
| 7.0 | 97.6 | 72.3 | 73.5 | 75.0 | 98.6 | 85.8 | 89.3 | 87.3 |

TABLE 8

Formulation stability- nicotine sulphate concentration results in pouches

| | Nicotine Sulphate | | | | | | | |
|---|---|---|---|---|---|---|---|---|
| Formulation | % Recovery (8 mg/mL) | | | | % Recovery (32 mg/mL) | | | |
| Theoretical pH | T = 0 | T = 7 days | T = 15 days | T = 28 days | T = 0 | T = 7 days | T = 15 days | T = 28 days |
| 3.0 | 100.3 | 94.9 | 96.9 | 102.4 | 98.1 | 101.2 | 100.2 | 99.0 |
| 4.0 | 99.5 | 95.4 | 98.3 | 100.9 | 98.4 | 97.0 | 98.3 | 99.0 |
| 5.0 | 100.4 | 95.6 | 95.2 | 98.5 | 98.5 | 97.8 | 99.0 | 98.0 |

TABLE 8-continued

Formulation stability- nicotine sulphate concentration results in pouches

Nicotine Sulphate

| Formulation | % Recovery (8 mg/mL) | | | | % Recovery (32 mg/mL) | | | |
|---|---|---|---|---|---|---|---|---|
| Theoretical pH | T = 0 | T = 7 days | T = 15 days | T = 28 days | T = 0 | T = 7 days | T = 15 days | T = 28 days |
| 6.0 | 100.2 | 94.3 | 92.5 | 94.0 | 99.3 | 94.6 | 95.0 | 95.8 |
| 7.0 | 97.6 | 75.0 | 75.2 | 82.2 | 99.0 | 89.6 | 89.4 | 90.1 |

Based on these results as well as theoretical calculations, pH 3.0 was chosen for use with polymeric products as the proportion of ionized species is maximized at this pH while maintaining acceptable safety profiles for an inhaled product.

Formulation Stability/Screening in AERx® Dosage Forms:

As buffering at extreme pH's is not desirable for inhaled products because it can elicit hyperreactivity, pH adjustment is preferred. For this reason an unbuffered formulation was evaluated.

AERx® dosage forms were filled with nicotine bitartrate and nicotine sulphate at both 10.7 and 32.0 mg/mL of nicotine and stored at 40° C./15% R.H. (accelerated storage condition recommended for semi-permeable containers, ICH Q1A) for a period of 14 days.

The results for pH (Table 9) and concentration (Table 10) indicated excellent control, confirming the choice of an unbuffered formulation. Having developed a robust formulation, we then proceeded to evaluate the dose titration capabilities as well as optimizing aerosol performance using these formulations.

Optimization of Aerosol Performance of Nicotine Formulation with the AERx® System Characterization and optimization of delivery efficiency (emitted dose) of nicotine formulations from AERx® in a simulated inhalation:

Efficiency of delivery of formulation from the AERx® System is expressed as emitted dose (ED). For ED quantification, a known dose of each nicotine formulation was loaded into AERx® Strips and then aerosolized onto standardized collection filters. The filters were rinsed thoroughly with the assay diluent. Spiking studies were conducted to verify that all of the nicotine was recovered from the filter. The amount of nicotine in the rinsate was quantified by HPLC.

The ED data was excellent for the partial extrusion as well as multiple concentrations dose reduction strategies evaluated. Emitted dose in percent at the three levels using the partial extrusion strategy was 20.4, 17.2 and 18.8 with standard deviations of 1.4, 0.8 and 1.0 respectively (see Table 11). The percent emitted dose for the successive concentrations of 32.0, 21.3 and 10.7 mg/mL was 60.0, 61.7 and 62.7 with the standard deviations being 3.0, 2.8 and 3.2 respectively (see Table 12).

TABLE 9

Nicotine in AERx ® strips (stored at 40° C./15% RH)

pH values

| Formulation | T = Initial | T = 7 days | T = 14 days |
|---|---|---|---|
| Nicotine Bitartrate (10.7 mg/mL, pH 3.0) | 3.0 | 2.9 | 2.9 |
| Nicotine Bitartrate (32.0 mg/mL, pH 3.0) | 3.0 | 3.0 | 2.9 |
| Nicotine Sulphate (10.7 mg/mL, pH 3.0) | 3.0 | 2.9 | 2.9 |
| Nicotine Sulphate (32.0 mg/mL, pH 3.0) | 3.0 | 2.9 | 2.9 |

TABLE 10

Recovery of nicotine in AERx ® strips stored at 40° C./15% RH

% Recovery (SD)

| Formulation | T = Initial | T = 7 days | T = 14 days |
|---|---|---|---|
| Nicotine Bitartrate (10.7 mg/mL, pH 3.0) | 98.9 (0.5) | 102.1 (0.3) | 99.3 (0.2) |
| Nicotine Bitartrate (32.0 mg/mL, pH 3.0) | 100.2 (0.8) | 100.2 (0.5) | 102.9 (6.5) |
| Nicotine Sulphate (10.7 mg/mL, pH 3.0) | 100.0 (0.4) | 100.5 (0.2) | 100.7 (1.1) |
| Nicotine Sulphate (32.0 mg/mL, pH 3.0) | 97.4 (2.3) | 100.6 (0.9) | 100.0 (0.7) |

TABLE 11

Emitted dose performance using partial dose settings using 32 mg/mL nicotine bitartrate

| DF# | Level 1 ED (% LC) | Level 2 ED (% LC) | Level 3 ED (% LC) | Total ED | % 1st shot | % 2nd shot | % 3rd shot |
|---|---|---|---|---|---|---|---|
| 1 | 18.7 | 14.7 | 18.7 | 52.2 | 35.8 | 28.3 | 35.9 |
| 2 | 20.8 | 17.1 | 20.2 | 58.1 | 35.8 | 29.4 | 34.8 |
| 3 | 18.3 | 17.2 | 18.8 | 54.2 | 33.7 | 31.7 | 34.6 |
| 4 | 19.9 | 17.1 | 18.8 | 55.8 | 35.7 | 30.6 | 33.7 |
| 5 | 21.2 | 17.2 | 20.0 | 58.4 | 36.3 | 29.4 | 34.2 |
| 6 | 20.6 | 18.2 | 19.3 | 58.1 | 35.4 | 31.4 | 33.2 |
| 7 | 19.9 | 17.7 | 18.3 | 55.8 | 35.6 | 31.6 | 32.8 |
| 8 | 18.3 | 17.5 | 18.3 | 54.2 | 33.8 | 32.3 | 33.9 |
| 9 | 22.8 | 17.4 | 19.5 | 59.8 | 38.2 | 29.1 | 32.6 |
| 10 | 20.6 | 17.6 | 19.4 | 57.7 | 35.7 | 30.6 | 33.7 |
| 11 | 20.3 | 17.0 | 19.1 | 56.4 | 36.1 | 30.1 | 33.8 |
| 12 | 22.0 | 17.1 | 20.5 | 59.6 | 37.0 | 28.6 | 34.4 |
| 13 | 20.6 | 17.4 | 17.8 | 55.8 | 36.9 | 31.2 | 31.9 |
| 14 | 21.0 | 17.1 | 17.7 | 55.8 | 37.6 | 30.7 | 31.7 |
| 15 | 20.4 | 17.7 | 18.8 | 56.9 | 35.8 | 31.1 | 33.1 |
| 16 | 20.3 | 16.9 | 17.3 | 54.5 | 37.3 | 31.0 | 31.7 |
| 17 | 22.2 | 17.3 | 17.9 | 57.4 | 38.6 | 30.1 | 31.2 |
| 18 | 21.6 | 18.3 | 18.7 | 58.7 | 36.9 | 31.2 | 31.9 |
| 19 | 20.2 | 17.8 | 20.5 | 58.4 | 34.6 | 30.4 | 35.0 |
| 20 | 17.5 | 15.4 | 16.8 | 49.7 | 35.2 | 31.0 | 33.7 |
| Mean | 20.4 | 17.2 | 18.8 | 56.4 | 36.1 | 30.5 | 33.4 |
| SD | 1.36 | 0.82 | 1.03 | 2.53 | 1.29 | 1.07 | 1.27 |

TABLE 12

Emitted dose performance of nicotine formulations at various concentrations

| ED # | Full Extrusion: ED (% LC) | | | Full Extrusion: ED (mg) | | |
|---|---|---|---|---|---|---|
| | 32.0 mg/mL Nicotine Bitartrate | 21.3 mg/mL Nicotine Bitartrate | 10.7 mg/mL Nicotine Bitartrate | 32.0 mg/mL Nicotine Bitartrate | 21.3 mg/mL Nicotine Bitartrate | 10.7 mg/mL Nicotine Bitartrate |
| 1 | 56.2 | 55.6 | 59.5 | 0.90 | 0.59 | 0.32 |
| 2 | 59.4 | 59.7 | 62.6 | 0.95 | 0.64 | 0.34 |
| 3 | 56.9 | 61.8 | 60.4 | 0.91 | 0.66 | 0.32 |
| 4 | 56.6 | 60.4 | 62.9 | 0.91 | 0.64 | 0.34 |
| 5 | 57.7 | 60.9 | 65.3 | 0.92 | 0.65 | 0.35 |
| 6 | 58.1 | 64.8 | 62.3 | 0.93 | 0.69 | 0.33 |
| 7 | 63.6 | 57.9 | 60.0 | 1.02 | 0.62 | 0.32 |
| 8 | 60.3 | 65.2 | 58.1 | 0.96 | 0.69 | 0.31 |
| 9 | 54.6 | 59.9 | 66.1 | 0.87 | 0.64 | 0.35 |
| 10 | 58.4 | 58.0 | 67.9 | 0.93 | 0.62 | 0.36 |
| 11 | 59.8 | 60.1 | 66.8 | 0.96 | 0.64 | 0.36 |
| 12 | 63.8 | 63.0 | 61.8 | 1.02 | 0.67 | 0.33 |
| 13 | 60.0 | 59.7 | 64.6 | 0.96 | 0.64 | 0.35 |
| 14 | 63.1 | 62.8 | 65.0 | 1.01 | 0.67 | 0.35 |
| 15 | 61.2 | 63.7 | 56.0 | 0.98 | 0.68 | 0.30 |
| 16 | 64.5 | 66.0 | 62.0 | 1.03 | 0.70 | 0.33 |
| 17 | 62.7 | 62.0 | 65.2 | 1.00 | 0.66 | 0.35 |
| 18 | 65.5 | 65.7 | 63.7 | 1.05 | 0.70 | 0.34 |
| 19 | 58.1 | 64.2 | 65.1 | 0.93 | 0.68 | 0.35 |
| 20 | 59.9 | 62.0 | 58.0 | 0.96 | 0.66 | 0.31 |
| Mean | 60.0 | 61.7 | 62.7 | 0.96 | 0.66 | 0.34 |
| SD | 3.0 | 2.8 | 3.2 | 0.05 | 0.03 | 0.02 |
| % RSD | 5.1 | 4.6 | 5.1 | 5.1 | 4.6 | 5.1 |

Development of Dose-Titration Capabilities

Partial Extrusion of a Single AERx® Strip

Partial extrusion of an AERx® Strip was carried out by altering the settings for the piston position, to program it to aerosolize only a portion of the contents of the AERx® Strip. Testing was done using nicotine formulations, with the results being presented in Table 11. The delivered dose in percent of emitted dose at the three levels was 36.1, 30.5 and 33.4 with standard deviations of 1.3, 1.1 and 1.3 respectively. This corresponds to a nicotine dose of 0.33 mg, 0.28 mg and 0.30 mg at the three dose levels respectively.

Altering the Concentration of Nicotine in AERx® Strip

The emitted dose and particle size distribution of nicotine formulations at various concentrations was evaluated. In order to keep the delivered dose constant, the range of concentrations tested were matched to the results of the aerosol performance studies from partial extrusion discussed above. Results are presented in Table 13. The percent emitted dose for the successive concentrations of 32.0, 21.3 and 10.7 mg/mL was 60.0, 61.7 and 62.7 with the standard deviations being 3.0, 2.8 and 3.2 respectively. The corresponding delivered nicotine dose at the three concentrations was calculated to be 0.96 mg, 0.66 mg and 0.34 mg with standard deviations of 0.05, 0.03 and 0.02 respectively.

Optimizing Particle Size Distribution of the Aerosol Droplets of Nicotine Formulations Generated Using AERx®

Particle size distribution (PSD) is a key determinant of the regional lung deposition of inhaled aerosols. A cascade impactor (Series 20-800 Mark II, Thermo Andersen), which size selectively collects the aerosol by inertial impaction on a series of stages, was used to characterize the aerosol PSD. The PSD was characterized in terms of Mass Median Aerodynamic Diameter (MMAD) and Geometric Standard Deviation ($\sigma g$). MMAD denotes the particle size at which half of the total aerosol mass is contained in larger particles and half in smaller particles. The $\sigma g$ indicates the variability of aerosol particle sizes. An aerosol composed of identical size particles would have a $\sigma g$ of 1.0; $\sigma g$ of $\leq 1.3$ is considered monodisperse; $\sigma g$ of $\geq 1.3$ is considered polydisperse.

We evaluated PSD with the optimized nicotine formulations. The MMAD ranged between 2.5-2.7 µm for the different combinations of device and formulation combinations (see Table 14). The GSD was 1.3, which indicates the monodispersity of the aerosol. The influence of PSD on nicotine kinetics, efficiency, and success rates with the product would need to be determined as part of the Phase II proposal. The

TABLE 13

Emitted dose summary

| Formulation | Type of Extrustion (N = 20) | % ED (SD) | Emitted Drug (mg) | Dose to the lung [$FPF_{3.5} = 0.78$] (mg) |
|---|---|---|---|---|
| 32.0 mg/mL Nicotine Bitartrate, pH 3.0 | Partial Dose Level 1 | 20.4 (1.36) | 0.33 | 0.26 |
| | Partial Dose Level 2 | 37.9 (1.96) | 0.61 | 0.48 |
| | Partial Dose Level 3 | 56.4 (2.53) | 0.90 | 0.71 |
| 10.7 mg/mL Nicotine Bitartrate, pH 3.0 | Full Extrusion | 62.7 (3.22) | 0.34 | 0.27 |
| 21.3 mg/mL Nicotine Bitartrate, pH 3.0 | Full Extrusion | 61.7 (2.82) | 0.66 | 0.51 |
| 32.0 mg/mL Nicotine Bitartrate, pH 3.0 | Full Extrusion | 60.0 (3.04) | 0.96 | 0.75 | fraction of particles under 3.5 μm is typically used to evaluate the fraction of aerosol capable of deposition in the deep lung. The typical fine particle fraction was about 80% (Table 14), indicating that the majority of the deposited aerosol was capable of deep lung deposition, key to the success of the therapy.

TABLE 14

Particle Size Distribution (PSD) summary

| Formulation | Type of extrusion (N = 3) | MMAD (SD) | GSD (SD) | $FPF_{8.6}$ |
|---|---|---|---|---|
| 32.0 mg/ml Nicotine Bitartrate, pH 3.0 | 3 partial extrusions | 2.66 (0.04) | 1.28 (0.01) | 0.779 |
| 32.0 mg/ml Nicotine Bitartrate, pH 3.0 | 1 partial extrusion | 2.65 (0.03) | 1.28 (0.01) | 0.783 |
| 32.0 mg/ml Nicotine Bitartrate, pH 3.0 | Full extrusions | 2.49 (0.04) | 1.35 (0.02) | 0.762 |

Characterization of Stability of Nicotine Formulations in AERx® Strip Dosage Forms In the following set of experiments, the stability of the selected nicotine formulations was evaluated in AERx® Strip dosage forms.

Physical and Chemical Characterization of the Selected Formulations and Aerosol Performance Upon Storage in AERx® Strips for Up to 1 Month:

The primary storage condition for the strips was chosen to be 25° C./40% R.H., as the formulation selected was quite simple and did not require refrigerated storage. The strips were loaded with 5 μL of nicotine formulation, sealed and stored at 25° C./40% R.H., as well as at the accelerated storage condition of 40° C./15% R.H. for up to 1 month. The formulations in the strips were characterized for concentration, pH and content uniformity, in addition to measurement of aerosol performance (emitted dose, particle size distribution) with the AERx® Strips in storage. The results from the one month stability study indicated maintenance of pH, concentration, as well as aerosol performance over the tested stability duration at the primary as well as accelerated storage condition (Tables 15 & 16). The emitted dose (ED) performance at both the concentrations was within normal variability. The MMAD was 2.4 and 2.8 to 2.9 for the two formulation strengths respectively; with GSD's of 1.3, indicating the monodispersity of the aerosol. The fine particle fraction under 3.5 μm was about 82% for the 10.7 mg/mL formulation and 72% for the 32.0 mg/mL formulation. A high fraction of the emitted aerosol in the respirable range ensures that majority of the aerosol will result in deep lung deposition. The data indicates acceptable stability of the formulations in AERx® strips for the duration of the stability study. In the next part of the development program, it will be important to finalize the final formulation concentrations (dependent on the chosen dose reduction and commercialization strategy) and generate stability data to support any proposed clinical studies.

TABLE 15

Summary for Nicotine Bitartrate, 10.7 mg/ml in Aerx ® strips

| Test Attributes | T = Initial | T = 4 weeks 25° C./40% RH | T = 4 weeks 40° C./15% RH |
|---|---|---|---|
| pH (% RSD) | 3.0 (0.2) | 3.1 (0.0) | 3.2 (0.4) |
| Concentration, mg/mL (% RSD) | 10.8 (0.8) | 10.7 (2.1) | 10.7 (0.3) |
| Content Uniformity Range, % LC (% RSD) | 97.0-100.0 (1.2) | N/A | N/A |
| Unit Dose, % LC (% RSD) | 99.1 (1.2) | 96.7 (1.7) | 96.5 (1.5) |
| Emitted Dose, % LC (% RSD) | 55.1 (4.9) | 52.0 (5.8) | 52.5 (3.0) |
| Emitted Dose Uniformity, % Mean ED (% RSD) | 95.2-107.0 (4.9) | 92.7-106.7 (5.8) | 95.5-102.9 (3.0) |
| Particle Size Distribution [Record: MMAD (μm), GSD, $FPF_{3.5}$, FPD (% LC)] | 2.41, 1.31, 0.81, 44.6 | 2.42, 1.27, 0.85, 44.2 | 2.43, 1.28, 0.82, 43.1 |

TABLE 16

Stability Summary for Nicotine Bitartrate, 32.0 mg/mL in AERx ® strips

| Test Attributes | T = Initial | T = 4 weeks 25° C./40% RH | T = 4 weeks 40° C./15% RH |
|---|---|---|---|
| pH (% RSD) | 3.0 (0.0) | 3.1 (0.5) | 3.1 (0.8) |
| Concentration, mg/mL (% RSD) | 32.5 (0.9) | 31.2 (1.0) | 31.5 (1.0) |
| Content Uniformity Range, % LC (% RSD) | 99.2-101.5 (0.8) | N/A | N/A |
| Unit Dose, % LC (% RSD) | 100.3 (0.8) | 96.7 (0.7) | 96.9 (0.5) |
| Emitted Dose, % LC (% RSD) | 58.3 (4.3) | 52.8 (3.1) | 55.9 (1.3) |
| Emitted Dose Uniformity, % Mean ED (% RSD) | 94.0-106.8 (4.3) | 95.6-103.1 (3.1) | 97.9-101.5 (1.3) |
| Particle Size Distribution [Record: MMAD (+m), GSD, $FPF_{3.5}$, FPD (% LC)] | 2.77, 1.27, 0.74, 43.1 | 2.87, 1.25, 0.70, 37.0 | 2.87, 1.25, 0.71, 39.7 |

CONCLUSION

The example above supports the feasibility of delivery of nicotine for smoking cessation using the AERx® System with an aqueous formulation that was stable at room temperature for a period of at least a month (duration of stability study). The typical MMAD of the aerosols using either dose reduction strategy was 2.6 μm, whereas the GSD was 1.3. The fine particle fraction was 80%, ensuring deposition of the majority of the emitted aerosol in the deep lung, mimicking smoking, and important for a successful smoking cessation product.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A system for tobacco-less nicotine treatment of a patient, the system comprising:
   a first and a second group of containers wherein each container of the first group confines a substantially identical pharmaceutically active, inhalable nicotine formulation, and each container of the second group confines a substantially identical pharmaceutically active, inhalable nicotine formulation that is physically, chemically or quantitatively different from the nicotine formulation confined in the first group of containers; and
   an inhaler configured to deliver the tobacco-less nicotine formulation confined in each container of the first group in a single inhalation,
   wherein the nicotine formulation is aerosolizable from pores on the first and second group of containers and wherein the first group of containers comprise a first pore pattern and the second group of containers comprise a second pore pattern wherein the first pore pattern produces a first aerosol and the second pore pattern produces a second aerosol different from the first aerosol.

2. The system of claim 1, wherein
   ii) the nicotine formulation of the first group of containers is sufficient to provide a peak nicotine arterial plasma concentration in the patient within 5 minutes of delivery; and,
   ii) the nicotine formulation of the second group of containers is sufficient to provide a sustained nicotine arterial plasma concentration in the patient for at least 60 minutes after delivery.

3. The system of claim 2, wherein the peak nicotine arterial plasma concentration is at least 10 ng/ml.

4. The system of claim 2, wherein the sustained nicotine arterial plasma concentration is at least 5 ng/ml.

5. The system of claim 1, further comprising:
   an additional compound in the formulation which compound is selected from the group consisting of an antidepressant and an anxiolytic.

6. The system of claim 5, wherein the additional compound is dissolved in the tobacco-less nicotine formulation.

7. The system of claim 5, wherein the additional compound is ingestable.

8. The system of claim 5, wherein the additional compound is inhalable.

9. The system of claim 5, wherein the nicotine formulation confined by the containers is a liquid.

10. The system of claim 1, wherein particles of the first aerosol have a smaller diameter than particles of the second aerosol.

11. The system of claim 1, wherein the first aerosol comprises a plurality of particles each particle having a diameter between about 1 μm and about 12 μm, wherein at least about 55% of the particles have a diameter between about 1 μm and about 4 μm.

12. The system of claim 1, wherein the first aerosol comprises a plurality of particles each particle having a diameter between about 1 μm and about 12 μm, wherein more than about 50% of the particles have a diameter between about 1 μm and about 4 μm.

13. The system of claim 1, wherein the inhaler is configured to deliver the nicotine formulation of each container in a single inhalation.

* * * * *